US009125385B2

(12) United States Patent
Luo et al.

(10) Patent No.: US 9,125,385 B2
(45) Date of Patent: Sep. 8, 2015

(54) SITE-DIRECTED INTEGRATION OF TRANSGENES IN MAMMALS

(75) Inventors: Liqun Luo, Palo Alto, CA (US); Ruby Yanru Tsai, San Jose, CA (US); Bosiljka Tasic, Palo Alto, CA (US); Simon Hippenmeyer, Menlo Park, CA (US); Hui Zong, Eugene, OR (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 228 days.

(21) Appl. No.: 13/293,890

(22) Filed: Nov. 10, 2011

(65) Prior Publication Data

US 2012/0124686 A1    May 17, 2012

Related U.S. Application Data

(60) Provisional application No. 61/413,257, filed on Nov. 12, 2010.

(51) Int. Cl.
*C12N 15/00* (2006.01)
*A01K 67/027* (2006.01)
*C12N 15/85* (2006.01)
*C12N 9/12* (2006.01)

(52) U.S. Cl.
CPC .......... *A01K 67/0275* (2013.01); *C12N 9/1241* (2013.01); *C12N 15/8509* (2013.01); *A01K 2217/072* (2013.01); *A01K 2217/206* (2013.01); *A01K 2227/105* (2013.01); *C12N 2795/00022* (2013.01); *C12N 2800/30* (2013.01)

(58) Field of Classification Search
USPC ....................................... 435/325; 800/21, 18
See application file for complete search history.

(56) References Cited

U.S. PATENT DOCUMENTS

| 2004/0003420 | A1 | 1/2004 | Kuhn et al. |
| 2005/0229263 | A1* | 10/2005 | Buelow ............................ 800/8 |
| 2006/0128020 | A1* | 6/2006 | Calos ............................ 435/456 |
| 2010/0190178 | A1 | 7/2010 | Calos et al. |

FOREIGN PATENT DOCUMENTS

WO          2009115295          9/2009

OTHER PUBLICATIONS

Belteki et al. (2003) Site-specific cassette exchange and germline transmission with mouse ES cells expressing phiC31 integrase. Nature Biotechnology 21: 321-324.*
Keravala et al. (2006) PhiC31 integrase mediates integration in cultured synovial cells and enhances gene expression in rabbit joints. The Journal of Gene Medicine 8: 1008-1017.*
Benoist et al. (1981) "In vivo sequence requirements of the SV40 early promotor region" Nature (London) 290:304-310.
Broach (1982) "The yeast plasmid 2μ circle" Cell 28:203-204.
Capecchi (1989) "Altering the genome by homologous recombination" Science 244(4910):1288-1292.
Gallardo et al. (2007) "Generation of a germ cell-specific mouse transgenic Cre line, Vasa-Cre" Genesis 45 (6):413-417.
Gribskov (1986) "Sigma factors from *E. coli, B. subtilis*, phage SP01, and phage T4 are homologous proteins" Nucl. Acids Res. 14(6):6745-6763.
Groth et al. (2000) "phage integrase directs efficient site-specific integration in human cells" Proc Natl Acad Sci U S A 97:5995-6000.
Hamer & Walling (1982) "Regulation in vivo of a cloned mammalian gene: cadmium induces the transcription of a mouse metallothionein gene in SV40 vectors" J. Mol. Appl. Gen. 1(4):273-288.
Hollis et al. (2003) "Phage integrases for the construction and manipulation of transgenic mammals" Reprod Biol. Endocrinol 1:79.
International Search Report for International Application No. PCT/US2011/060209, dated Mar. 21, 2012.
Johnston et al. (1982) "Isolation of the yeast regulatory gene GAL4 and analysis of its dosage effects on the galactose/melibiose regulon" Proc. Natl. Acad. Sci. (USA) 79(22):6971-6975.
McKnight (1982) "Functional relationships between transcriptional control signals of the thymidine kinase gene of herpes simplex virus" Cell 31(2 pt 1):355-365.
Meyer M et al. (2010) "Gene targeting by homologous recombination in mouse zygotes mediated by zinc-finger nucleases" Proc Natl Acad Sci U S A 107(34):15022-15026.
Nagy et al. (1993) "Derivation of completely cell culture-derived mice from early-passage embryonic stem cells" Proc Natl Acad Sci U S A 90(18):8424-8428.
Okada et al. (1999) "Imaging cells in the developing nervous system with retrovirus expressing modified green fluorescent protein" Exp Neurol 156(2):394-406.
Raymond & Soriano (2007) "High-efficiency FLP and PhiC31 site-specific recombination in mammalian cells" PLoS One 2(1):e162.
Seibler et al. (1998) "DNA cassette exchange in ES cells mediated by Flp recombinase: an efficient strategy for repeated modification of tagged loci by marker-free constructs" Biochemistry 37(18):6229-6234.

(Continued)

*Primary Examiner* — Michael Wilson
(74) *Attorney, Agent, or Firm* — Edward J. Baba; Shweta Chandra; Bozicevic, Field & Francis LLP

(57) ABSTRACT

The present disclosure provides a method of making a mammal (e.g., a rodent, such as a mouse) by integrating an intact polynucleotide sequence into a specific genomic locus of the mammal to result in a transgenic mammal. A transgenic mammal made by the methods of the present disclosure would contain a known copy number (e.g., one) of the inserted polynucleotide sequence at a predetermined location. The method involves introducing a site-specific recombinase and a targeting construct, containing a first recombination site and the polynucleotide sequence of interest, into the mammalian cell. The genome of the cell contains a second recombination site and recombination between the first and second recombination sites is facilitated by the site-specific, uni-directional recombinase. The result of the recombination is site-specific integration of the polynucleotide sequence of interest in the genome of the mammal. This inserted sequence is then also transmitted to the progeny of the mammal.

16 Claims, 11 Drawing Sheets

(56) References Cited

OTHER PUBLICATIONS

Siemering et al. (1996) "Mutations that suppress the thermosensitivity of green fluorescent protein" Curr Biol 6 (12):1653-1663.
Silver et al. (1984) "Amino terminus of the yeast GAL4 gene product is sufficient for nuclear localization" Proc. Natl. Acad. Sci. (USA) 81(19):5951-5955.
Soriano (1999) "Generalized lacZ expression with the ROSA26 Cre reporter strain" Nat Genet 21(1):70-71.
Srinivas et al. (2001) "Cre reporter strains produced by targeted insertion of EYFP and ECFP into the ROSA26 locus" BMC Dev Biol 1:4.
Hippenmeyer et al. (2010) "Genetic Mosaic Dissection of Lis1 and Ndel1 in Neuronal Migration" Neuron 68:695-709.
Tasic et al. (2011) "Site-specific integrase-mediated transgenesis in mice via pronuclear injection" PNAS 108 (19)7902-7907.
Zhu et al. (2013) "DICE, an efficient system for iterative genomic editing in human pluripotent stem cells" Nucleic Acids Research, pp. 1-13.

* cited by examiner

SITE-DIRECTED INTEGRATION OF TRANSGENES IN MAMMALS

CROSS-REFERENCE TO RELATED APPLICATIONS

This application claims the benefit of U.S. Provisional Application No. 61/413,257, filed on Nov. 12, 2010, which is herein incorporated by reference in its entirety.

STATEMENT REGARDING FEDERALLY SPONSORED RESEARCH

This invention was made with government support under federal grant nos. R01-NS050835 awarded by the National Institutes of Health. The United States Government has certain rights in this invention.

INTRODUCTION

Efficient and site-specific integration of DNA into the chromosomes of higher organisms is important for advances in basic and applied biology. Production of transgenic mice via microinjection of DNA into zygotic pronuclei has served mammalian genetics for many years. Although still the predominant method used to produce transgenic mice, this method has several limitations: the insertion site, integrity and copy number of the transgene cannot be controlled. The insertion into different chromosomal loci at random could disrupt the function of endogenous genes and subjects the transgenes to the local chromatin environment that can lead to transgene silencing or ectopic expression. In addition, the transgenic DNA concatemerized into a large array is subject to repeat-induced gene silencing.

Although one could resort to targeting the transgene to a specific chromosomal locus via homologous recombination in embryonic stem (ES) cells, such methods are laborious and time-consuming, as they involve creation of modified ES cells and mouse chimeras, as well as eventual germline transmission of the transgene.

SUMMARY

The present disclosure provides a method of making a transgenic mammal (e.g., a rodent, such as a mouse) by integrating an intact polynucleotide sequence into a specific genomic locus of the mammal to result in a transgenic mammal. A transgenic mammal made by the methods of the present disclosure would contain a known copy number (e.g., one) of the inserted polynucleotide sequence at a predetermined location. In some embodiments, the method involves introducing a unidirectional site-specific recombinase and a targeting construct, containing a first unidirectional recombination site and a polynucleotide sequence of interest, into a mammalian cell. The genome of the cell contains a second unidirectional recombination site and recombination between the first and second unidirectional recombination sites is facilitated by a unidirectional site-specific recombinase. The result of the recombination is site-specific integration of the polynucleotide sequence of interest in the genome of the mammal. This inserted sequence is then also transmitted to the progeny of the mammal.

In some embodiments, a targeting construct contains a polynucleotide sequence of interest flanked by unidirectional recombination sites, and the genome of the cell contains two or more unidirectional recombination sites, and a recombination reaction results in a cassette exchange wherein a portion of a nucleic acid sequence is integrated into the genome of a cell.

In some embodiments, the unidirectional recombinase used to incorporate the transgene into the genome of the mammal includes those that catalyze unidirectional integration. Examples are phage recombinases such as integrases ϕC31, TP901-1, and R4, wild-type or variations thereof.

In some embodiments, the methods of the present disclosure involve removing at least a portion of the nucleic acid sequence following its integration into the genome of a cell. In such embodiments, the targeting construct may further comprise an additional recombination site located 3' to a coding sequence of interest and the genome of the cell may further comprise an additional recombination site located 3' to a primary unidirectional recombination site. In some embodiments, the additional recombination site is a unidirectional recombination site or a bidirectional recombination site, and a portion of the nucleic acid sequence is removed using a corresponding unidirectional or bidirectional recombinase.

In some embodiments, the unidirectional recombination sites present in the nucleic acid containing a transgene of interest and in the locus of the mammal include, but are not limited to, wild-type attB, wild-type attP, pseudo-attB, pseudo-attP, and any tandem repeat combinations thereof. Additional pseudo-sites may be identified in the genome of essentially any target mammal, including, but not limited to, human and rodent cells and can be applied in the methods of the present disclosure.

The present disclosure further provides transgenic mammals that have a transgenic sequence and/or the substrate sequence of a site-directed recombinase inserted into a known locus, such as the Rosa26 (R26) locus on mouse chromosome 6 and/or an intergenic Hipp11 (H11) locus on mouse chromosome 11.

These and other embodiments of the present invention will readily occur to those of ordinary skill in the art in view of the disclosure herein.

DESCRIPTION OF THE DRAWINGS

The accompanying drawings, which are incorporated herein, form part of the specification. Together with this written description, the drawings further serve to explain the principles of, and to enable a person skilled in the relevant art(s), to make and use the present invention.

or the attB-pCA-GFP minicircle (right branch). The corresponding modified loci are: H11P3-pCA-GFP-BB (left) and H11P3-pCA-GFP (right), respectively. (Panel $C_2$) PCR results confirming site-specific integration, as explained in (Panel $B_2$). (Panel D) GFP expression in F2 mouse embryos at the embryonic day 11 (E11). Each row shows representative embryos from a single pregnancy with genotypes designated above. Images were obtained under identical conditions, except that "5×-exp" designates five-fold longer exposure time than for the rest of the images. The insets in top right corners represent the corresponding bright field images of each embryo.

Figure 2:
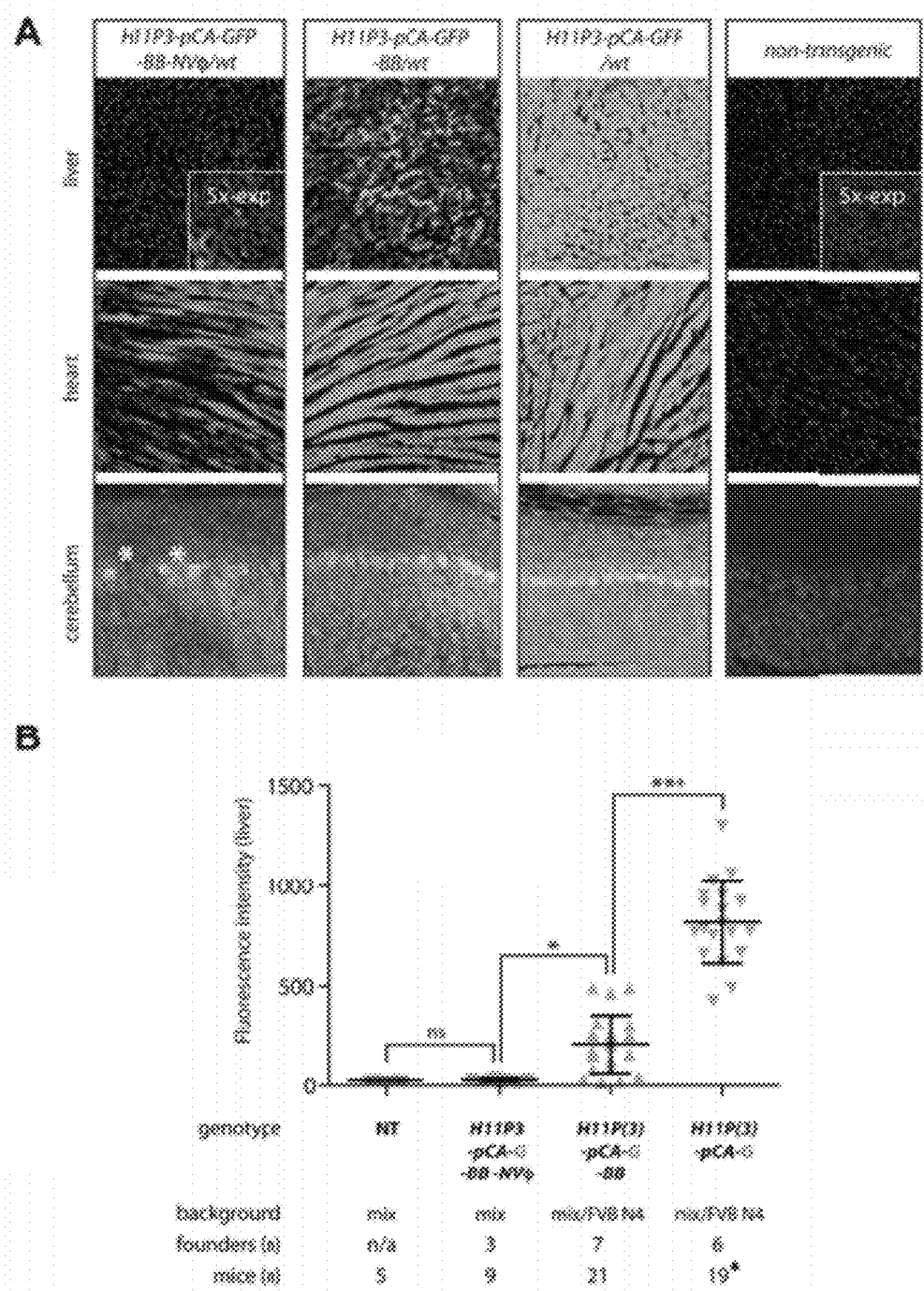

FIG. 2. GFP expression in adult animals carrying site-specific pCA-GFP transgenes introduced by ϕC31 integrase-mediated transgenesis. Panel A shows representative fluorescence microscopy images from liver, heart and cerebellum of F1 or F2 animals for the genotypes shown on top. Panel B shows average fluorescence in the GFP channel for liver sections of the genotypes shown below. The number of individual animals and founders analyzed for each genotype are listed below the genotypes. When samples from multiple founders were combined to obtain an average, each founder was represented by the same number of animals except in the case labeled by a spade. Statistical significance was calculated with ANOVA and post-hoc pairwise Tukey's test. ns, not significant; *, $p<0.05$; ***, $p<0.001$. Each set of data was represented by a mean±standard deviation. NT, non-transgenic.

Figure 3:
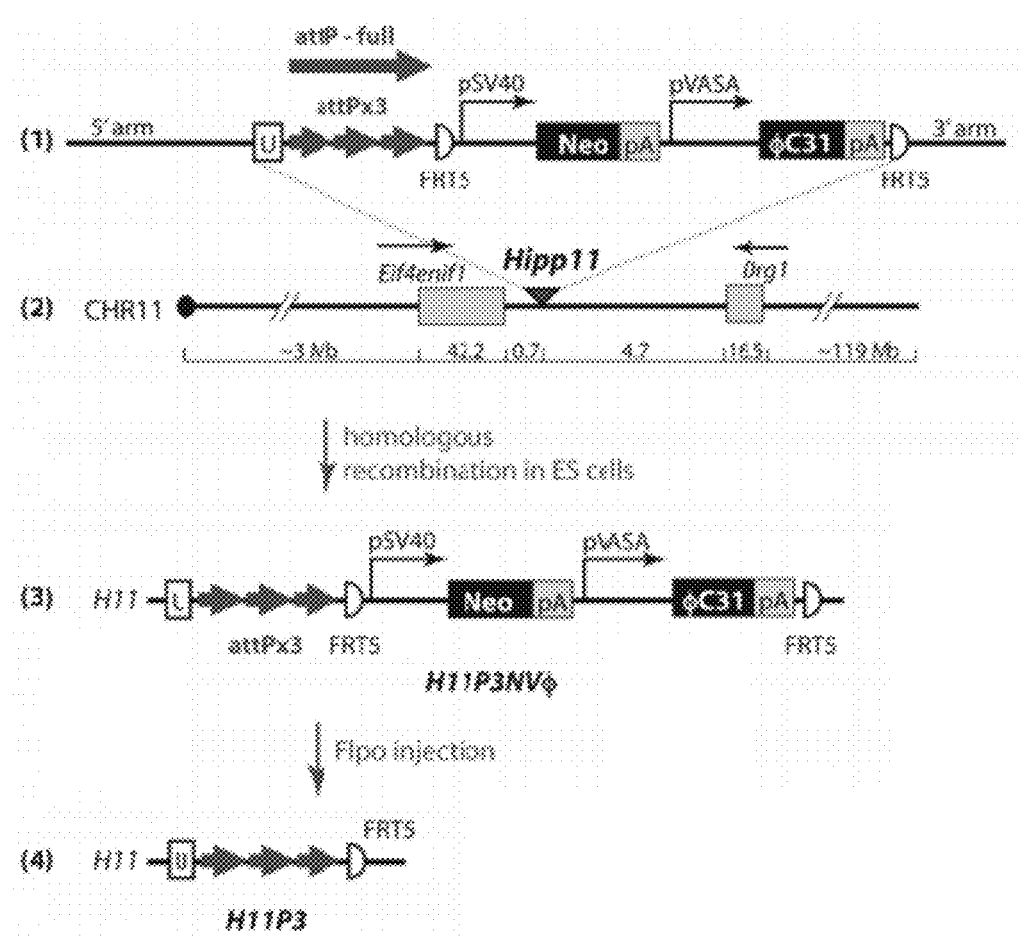

FIG. 3. Generation of H11 knockin alleles containing ϕC31 attP sites.

Figure 4:
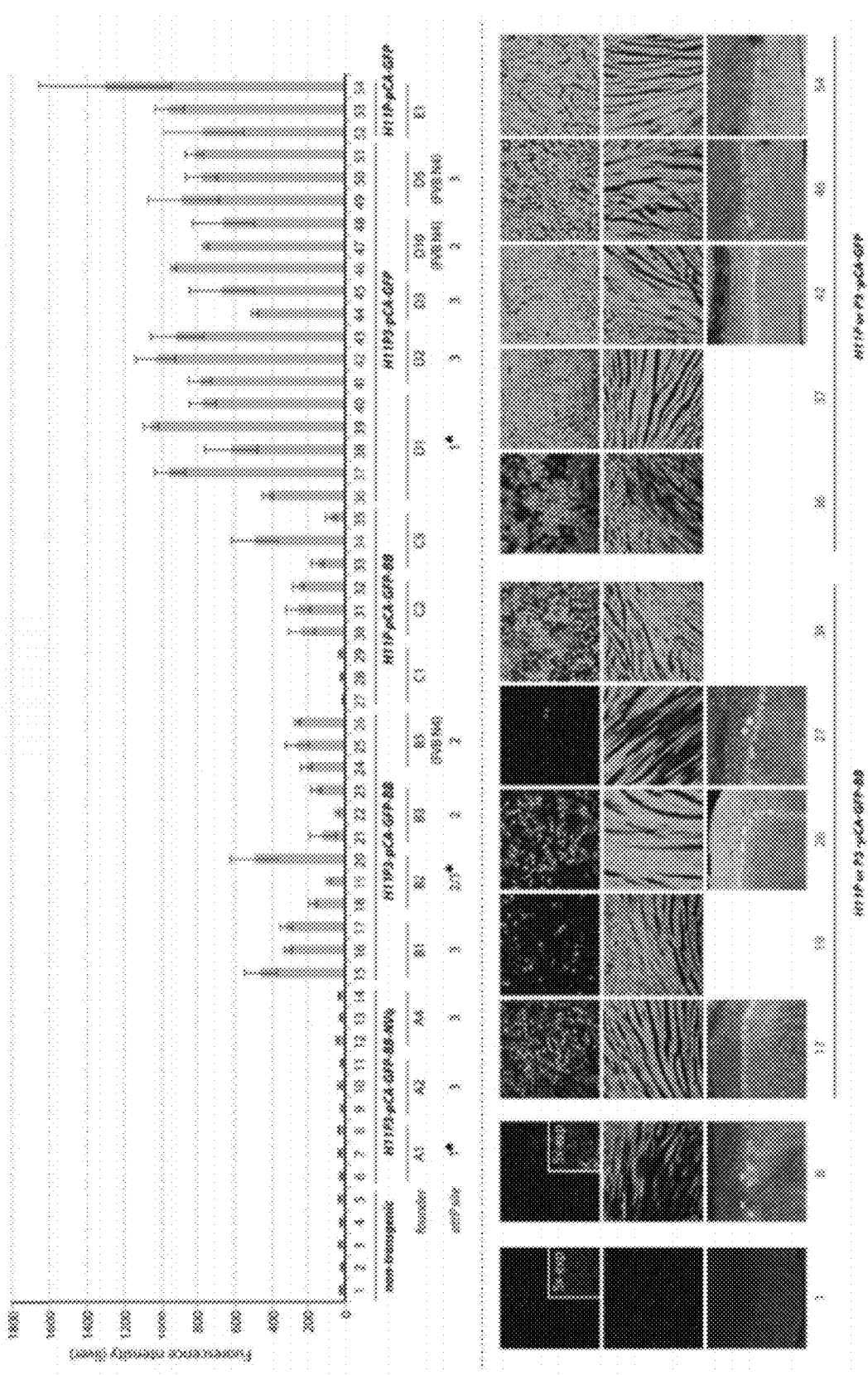

FIG. 4. GFP expression in individual adult animals carrying pCA-GFP site-specific transgenes introduced by ϕC31 integrase-mediated transgenesis. The graph represents average intensity of expression in the liver of each animal.

Figure 5:
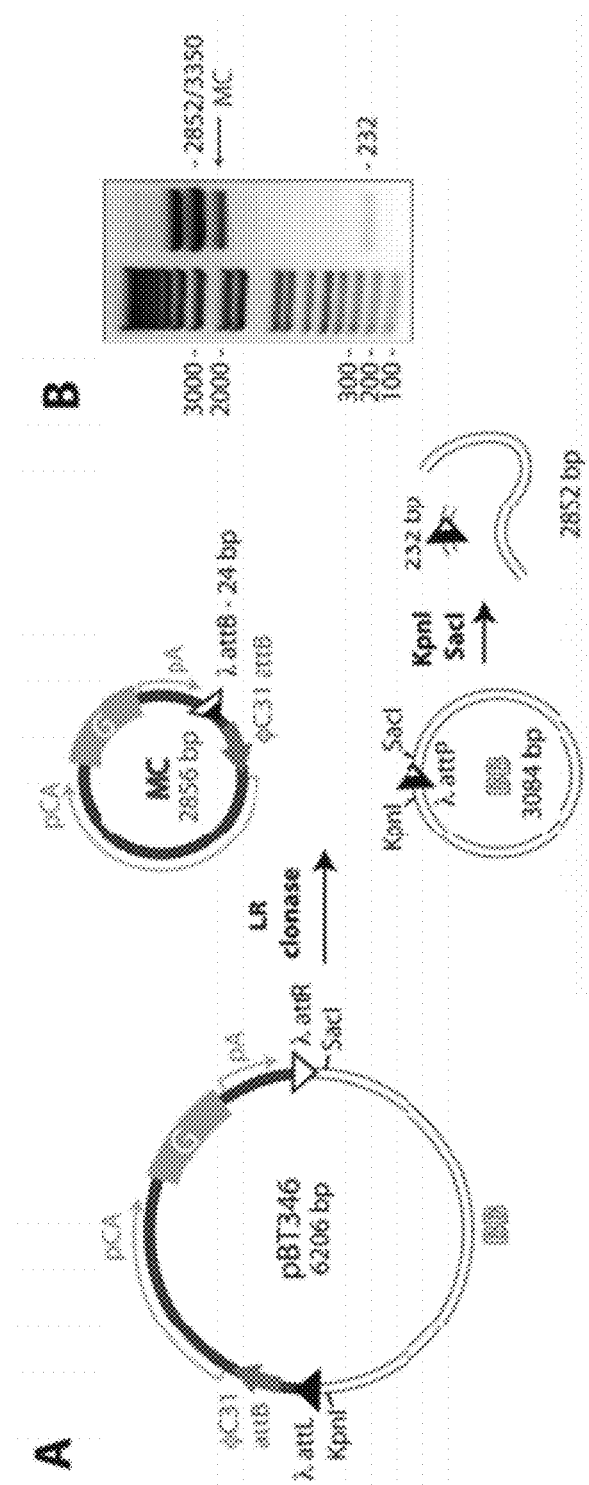

FIG. 5. Generation of minicircle DNA with λ integrase and excisionase (LR clonase, Invitrogen) in vitro. (Panel A) From left to right: The starting plasmid (pBT346) contains λ attL and attR sites, which recombine in the LR clonase-catalyzed reaction to generate two minicircles: one (MC) contains the ϕC31 attB site and pCA-GFP, and the other contains the plasmid bacterial backbone (BB). After recombination, the DNA is treated with appropriate restriction endonucleases to selectively digest the BB minicircle and the starting plasmid. (Panel B) The recombined and digested DNA is run on 1% agarose gel. MC DNA (indicated by the left-pointing arrow on the far right, labeled MC) migrates faster than the linear BB or plasmid DNA and is purified from the gel for microinjection.

Figure 6:
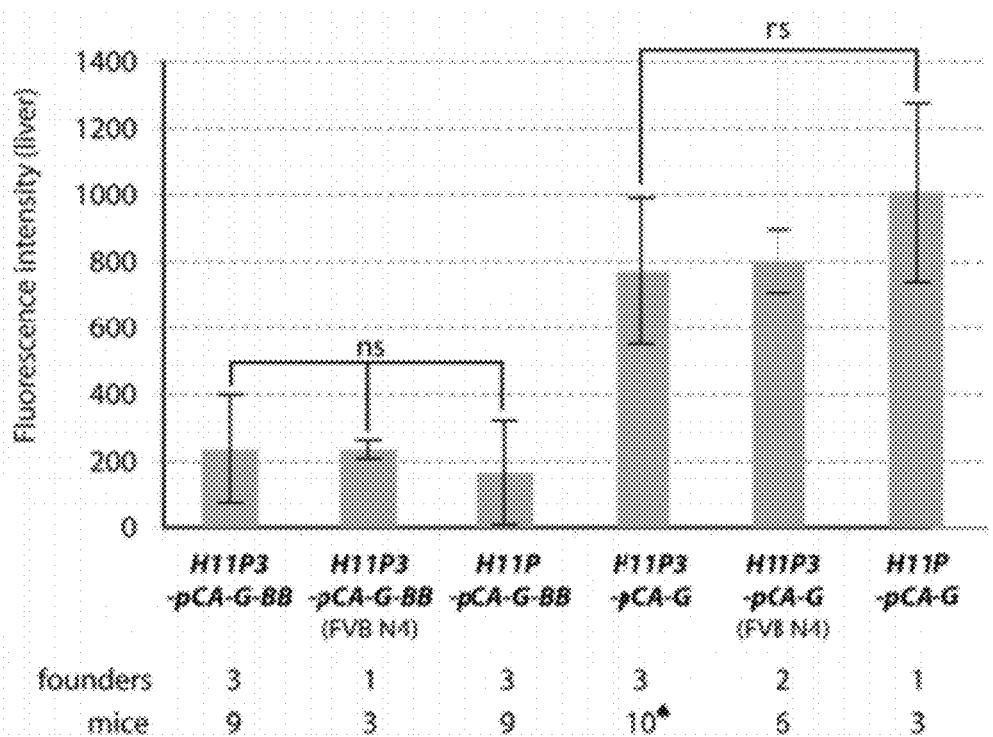

FIG. 6. Average GFP fluorescence in livers does not differ between mice containing an insertion into one of the 3 attP sites from H11P3 or insertion into a single site from H11P (compare $1^{st}$ vs. $3^{rd}$ column, and $4^{th}$ vs. $6^{th}$ column).

Figure 7:
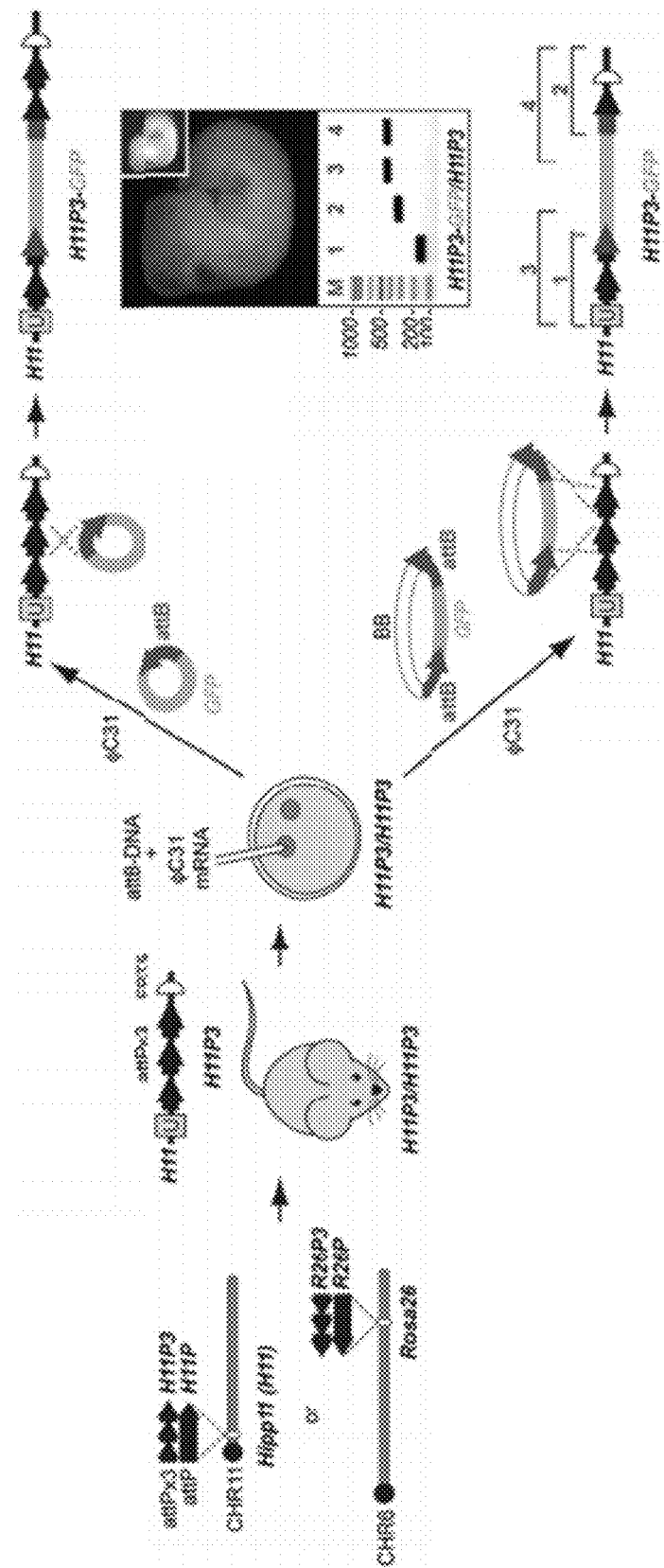

FIG. 7. Schematic summary for site-specific ϕC31 integrase-mediated transgenesis via pronuclear injection in mice. A single or three tandem attP sites were knocked into the Hipp11 (H11) or Rosa26 loci via homologous recombination in ES cells (left; additional details in FIG. 10). Mice homozygous for one of the modified loci (H11 is shown as an example) served as embryo donors. A mix of DNA and in vitro transcribed ϕC31 mRNA was injected into a single pronucleus of each zygote. The integration of plasmid bacterial backbone (BB) that decreases the transgene expression was avoided either by injecting a minicircle DNA with a single attB site (top branch; in this case, ϕC31 catalyzes a typical integration reaction), or by injecting plasmid DNA where the gene of interest (e.g., GFP) was flanked by two attB sites (bottom branch; in this case, ϕC31 catalyzes a recombinase-mediated cassette exchange reaction). Right, Center: A representative transgenic F0 embryo and the corresponding PCR results that indicate site-specific insertion. The numbers for the PCR results correspond to the numbers on the H11P3-pCA-GFP transgene scheme below; the same PCR tests can be used for the transgene above. The particular embryo shown was obtained by cassette exchange. Inset: Bright-field image of the same embryo.

Figure 8:
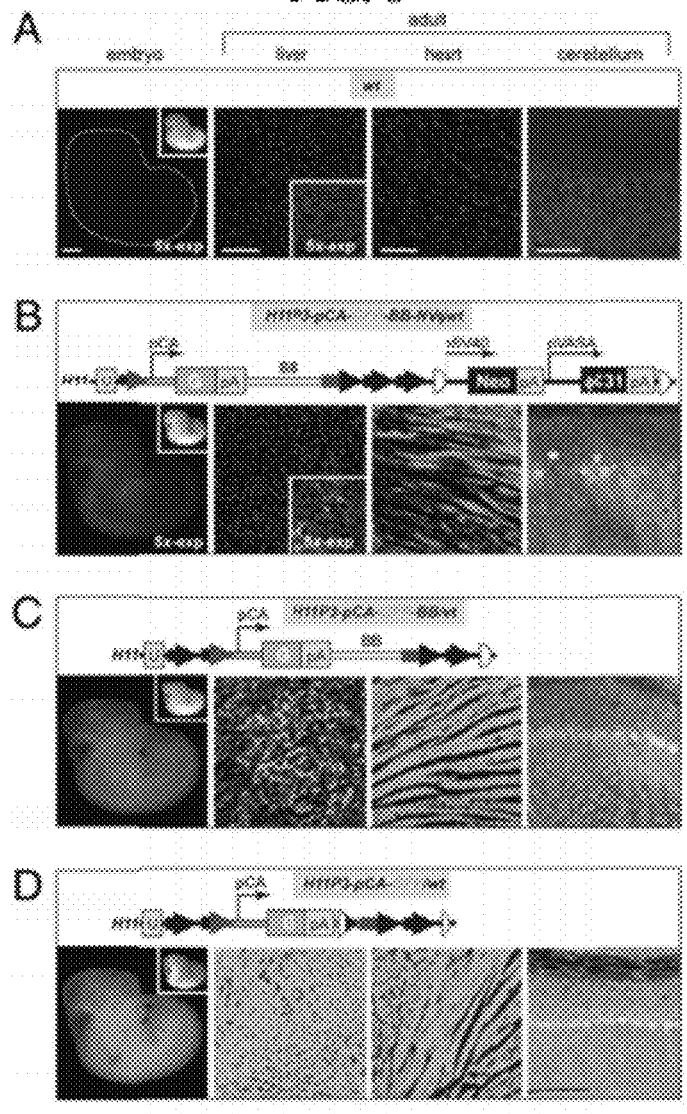

FIG. 8. GFP expression in animals carrying site-specific pCA-GFP transgenes introduced by ϕC31 integrase-mediated transgenesis. Panels A-D show representative fluorescence images from embryonic day 11 embryos and adult livers, hearts, and cerebella of N1 or N2 transgenic animals corresponding to the genotypes and schematics of transgenes shown (Upper portion of each panel). Embryos or same tissues were imaged under identical conditions, except that "5×-exp" designates fivefold longer exposure time than for the rest of the images in the same column. Whole-mount embryos were imaged for GFP fluorescence; corresponding bright-field images of each embryo are also shown (Insets). The livers and hearts are represented by epifluorescence images of 10 μm sections stained only by DAPI. The visible signal is GFP fluorescence. The cerebella are represented by confocal images of sections stained by anti-GFP antibody, anti-calbindin for Purkinje cells, and DAPI. Two Purkinje cells labeled by asterisks appear negative for GFP. ϕC31 attL and attR are the product of recombination of an attP (black arrows) and attB site. Half circles represent FRT5 sites. Half white/half black triangle represent λ-integrase attB site created during minicircle production. pSV40, SV40 promoter. pVASA, VASA promoter. U, unique sequence. pCA, CMV enhancer and β-actin promoter. G, GFP. pA, polyA signal. BB, plasmid bacterial backbone. (Scale bars: 1 mm for embryos, 100 μm for tissue sections.)

Figure 9:
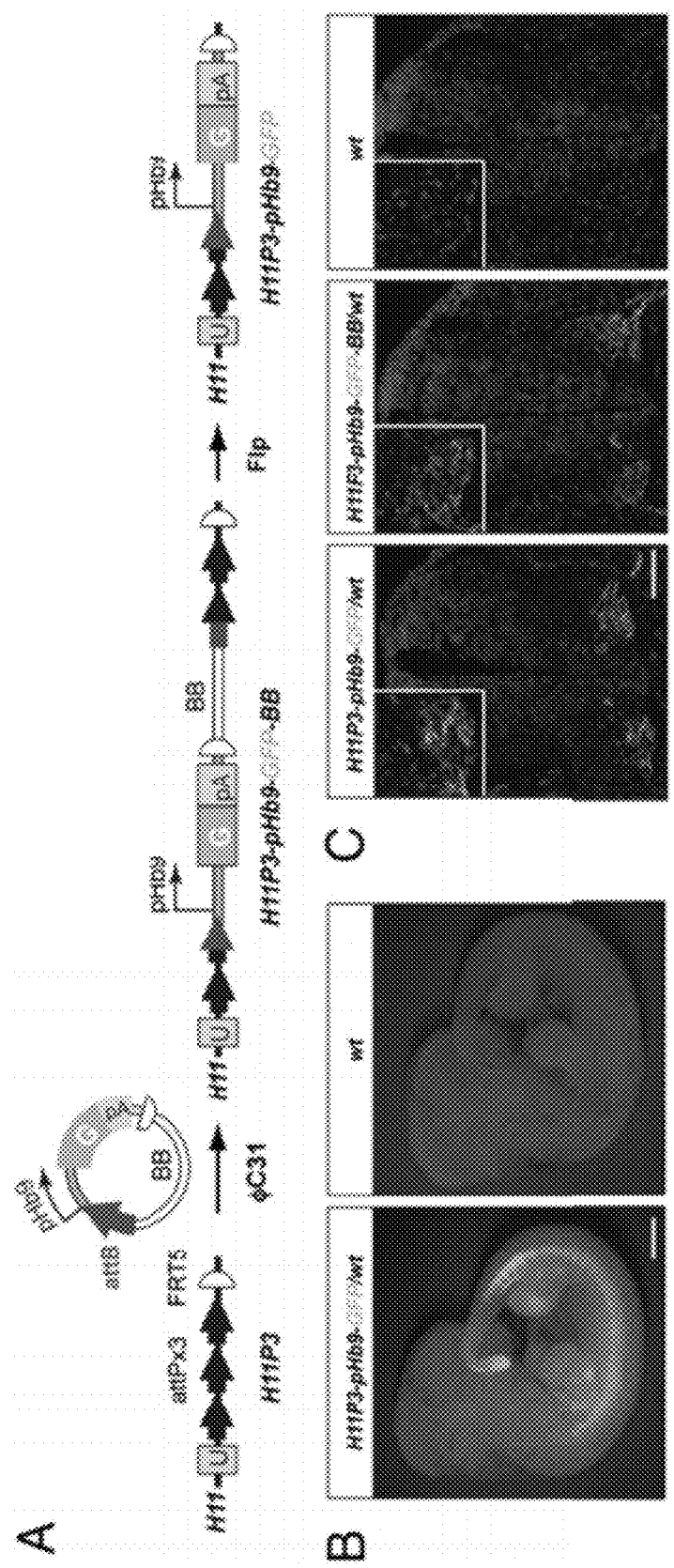

FIG. 9. GFP expression in embryos carrying a single copy of pHb9-GFP transgene site-specifically integrated in H11. (Panel A) Schematic representation of the generation of H11P3-pHb9-GFP allele. After site-specific integration of the plasmid pBT366, the bacterial backbone (BB) was removed by crossing to the GFP-FLPo transgenic line. The embryos that inherited only the Hb9 allele but not the Flpo transgene were tested for GFP expression. (Panel B) GFP expression in a whole-mount representative embryonic day 11 embryo containing the H11P3-pHb9-GFP allele. A wt littermate is also shown (Right). (Scale bar, 1 mm.) (Panel C) Immunofluorescence of section from embryonic day 11 spinal cords at limb level with anti-GFP signal, anti-Hb9, and DAPI. Insets: Magnified bottom left portions of each image containing Hb9-positive nuclei. (Scale bar, 100 μm.)

Figure 10:
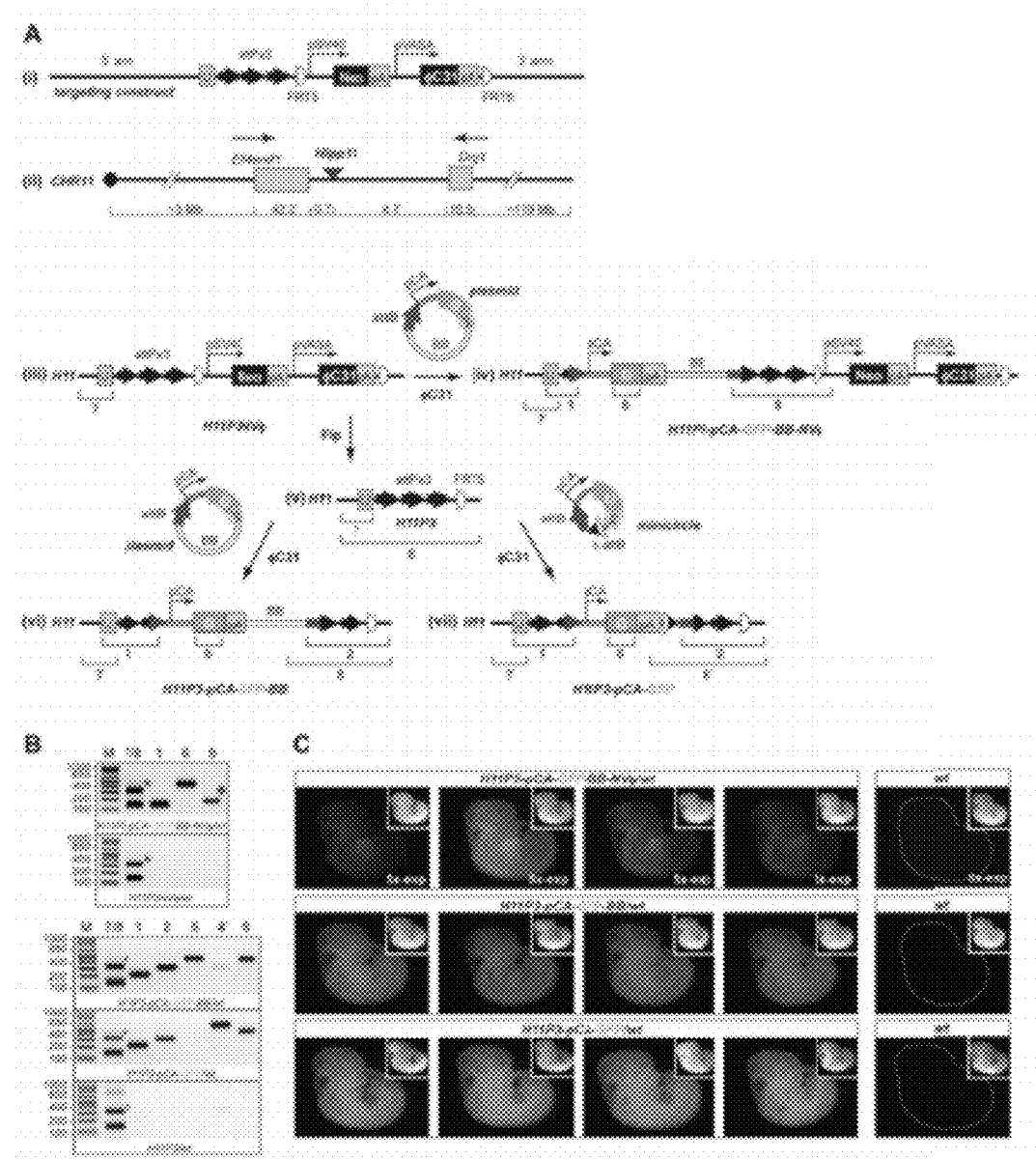

FIG. 10. (Panel A) Generation of H11 knockin alleles containing ϕC31 attP sites. (i) A schematic of the recombinant DNA construct for introduction of three attP sites and the NVϕ cassette into H11 via homologous recombination in mouse ES cells. Two versions, containing either a single "full-length" attP site or three tandem short attP sites, were generated. (ii) Mouse chromosome 11 with the Hipp11 (H11) locus designated as a triangle. The scale below is in kilobases, except where megabases (Mb) are indicated. (iii) The H11P3NVϕ allele resulting from homologous catalyzed site-specific insertion of the pattB-pCA-GFP plasmid (pBT316) into the first attP site. All three attP sites are suitable recipients for the transgene and the site used in any particular case can be determined by PCR. (v) H11P3 locus that was generated from (iii) by Flpo mRNA injection into the cytoplasm of mouse embryos carrying (iii). The H11 locus with a single attP site and the Rosa26 locus with either a single or three attP sites were generated in the same manner. (vi) and (vii), Two products obtained by φC3'-catalyzed site-specific insertion of the pattB-pCA-GFP plasmid (pBT316, left) or the attB-pCA-GFP minicircle (generated from pBT346, right). The corresponding alleles are: H11P3-pCA-GFP-BB (left) and H11P3-pCA-GFP (right), respectively. (Panel B) PCR results on N1 animals confirming site-specific integrations. The DNA template for each PCR panel was obtained from a mouse of the genotype designated below each gel. The numbers correspond to the PCR products designated on the schemes by red brackets and numbers in (Panel A). The primer set #9 amplified a band smaller than expected due to the deletion of two attP sites during integration (spade). The wt H11 locus is also amplified by primer set #8 to generate a 321 bp band (asterisk, see schematic (v)). (Panel C) GFP expression in N2 mouse embryos at embryonic day 11. Each row shows representative embryos from a single pregnancy with genotypes designated above. Images were obtained under identical conditions, except that "5×-exp" designates five-fold longer exposure time than for the rest of the images. Insets represent the corresponding bright field images of each embryo. Abbreviations: pSV40, SV40 promoter; pVASA, VASA promoter; U, unique sequence; FRT5, a mutant version of FRT that is compatible with itself but not with wt FRT; pCA, β-actin promoter and CMV enhancer; G, GFP; pA, polyA signal; BB, plasmid bacterial backbone; attB and attP, φC31 attB and attP sites.

Figure 11:
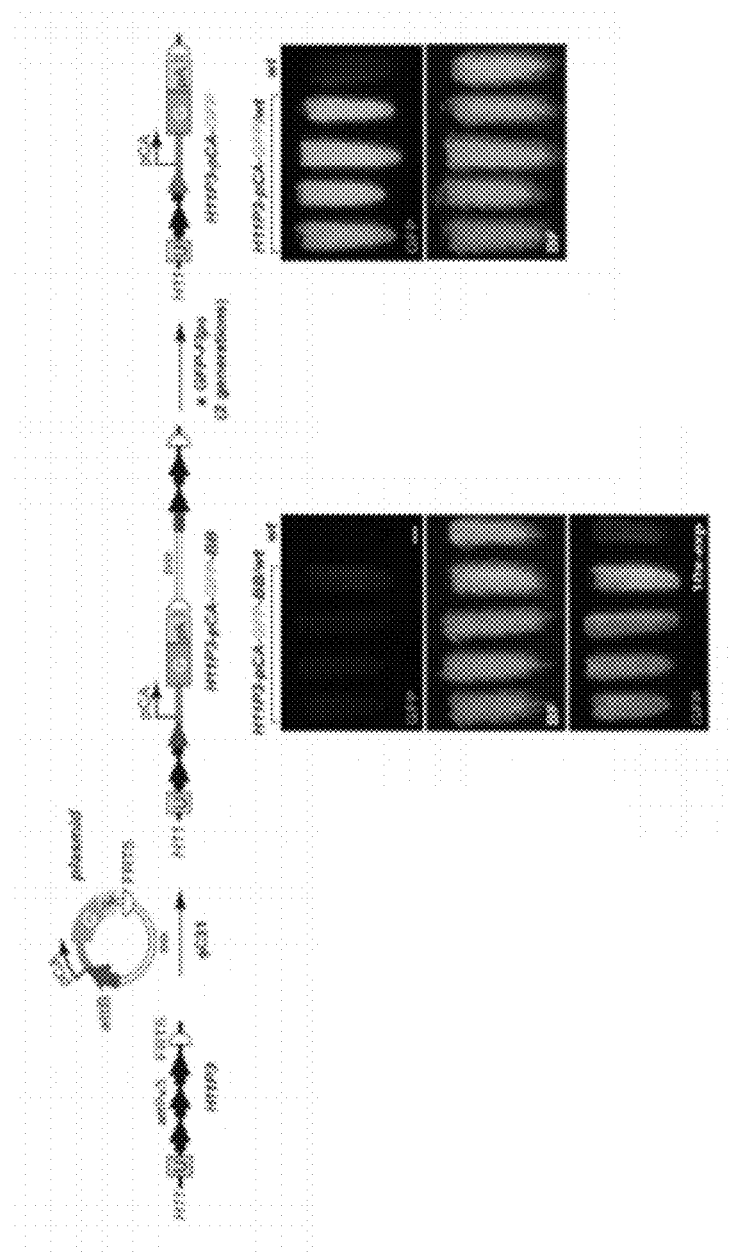

FIG. 11. GFP expression from a site-specifically integrated H11P3-pCA-GFP-BB transgene increases upon the removal of the bacterial backbone. Top, schematic of the generation of the H11P3-pCA-GFP-BB transgene (from pBT344) and subsequent derivation the H11P3-pCA-GFP transgene from it, by crossing to the GFP-Flpo transgenic mouse to remove the bacterial backbone. Below, four tail tips for each genotype designated above and a tail tip of a wt littermate were imaged for GFP fluorescence using identical imaging conditions. Bright field (BF) images of the same tails are shown further below. 10×-exp, the same tails above were imaged for GFP fluorescence with 10-times longer exposure. Scale bar, 1 mm.

DEFINITIONS

The following abbreviations may be used herein: pSV40, SV40 promoter; pVASA, VASA promoter; U, unique sequence; FRT5, a mutant version of FRT that is compatible with itself but not with wt FRT; pCA, β-actin promoter and CMV enhancer; G, GFP; pA, polyA signal; BB, plasmid's bacterial backbone; MC, minicircle; attB and attP, φC31 integrase attB and attP sites.

"Recombinases" are a family of enzymes that mediate site-specific recombination between specific DNA sequences recognized by the enzymes. Examples include Cre, and φC31.

"Uni-directional recombinases" or "integrases" refer to recombinase enzymes whose recognition sites are destroyed after the recombination has taken place. In other words, the sequence recognized by the recombinase is changed into one that is not recognized by the recombinase upon recombination. As a result, once a sequence is subjected to recombination by the recombinase, the continued presence of the recombinase cannot reverse the previous recombination event.

In particular, recombinases can recognize endogenous sequences in a genome of interest.

A "pseudo-site" is a DNA sequence recognized by a recombinase enzyme such that the recognition site differs in one or more base pairs from the wild-type recombinase recognition sequence and/or is present as an endogenous sequence in a genome that differs from the genome where the wild-type recognition sequence for the recombinase resides.

"Pseudo attP site" or "pseudo attB site" refer to pseudo sites that are similar to wild-type phage or bacterial attachment site sequences, respectively, for phage integrase enzymes. "Pseudo att site" is a more general term that can refer to either a pseudo attP site or a pseudo attB site.

A recombination site "native" to the genome, as used herein, means a recombination site that occurs naturally in the genome of a cell (i.e., the sites are not introduced into the genome, for example, by recombinant or transgenic means).

As used herein, "locus" refers to a specific location on a chromosome. A known locus can contain known genetic information, such as one or more polymorphic marker sites.

By "nucleic acid construct" it is meant a nucleic acid sequence that has been constructed to comprise one or more functional units not found together in nature. Examples include circular, double-stranded, extrachromosomal DNA molecules (plasmids), cosmids (plasmids containing COS sequences from lambda phage), viral genomes comprising non-native nucleic acid sequences, and the like.

As used herein, "nucleic acid fragment of interest" or "polynucleotide sequence of interest" refers to any nucleic acid fragment that one wishes to insert into a genome. Examples of nucleic acid fragments of interest include any genes (e.g., protein-encoding), such as therapeutic genes, marker genes, control regions, trait-producing fragments, and the like.

Methods of transforming cells are well known in the art. By "transformed" it is meant a heritable alteration in a cell resulting from the uptake of foreign DNA. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: www.ncbi.nlm.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.)

A first polynucleotide is "derived from" a second polynucleotide if it has the same or substantially the same basepair sequence as a region of the second polynucleotide, its cDNA, complements thereof, or if it displays sequence identity as described above.

"Derived from" in the context of an amino acid sequence or polynucleotide sequence (e.g., an amino acid sequence "derived from" a wild-type attP) is meant to indicate that the polypeptide or nucleic acid has a sequence that is based on that of a reference polypeptide or nucleic acid (e.g., a naturally occurring φC31 or encoding nucleic acid), and is not meant to be limiting as to the source or method in which the protein or nucleic acid is made.

A first polypeptide is "derived from" a second polypeptide if it is (i) encoded by a first polynucleotide derived from a second polynucleotide, or (ii) displays sequence identity to the second polypeptides as described above.

In the present disclosure, when a recombinase is "derived from a phage" the recombinase need not be explicitly produced by the phage itself, the phage is simply considered to be the original source of the recombinase and coding sequences thereof. Recombinases can, for example, be produced recombinantly or synthetically, by methods known in the art, or alternatively, recombinases may be purified from phage infected bacterial cultures.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The following detailed description of the figures refers to the accompanying drawings that illustrate an exemplary embodiment of an analyte measurement system. Other embodiments are possible. Modifications may be made to the embodiment described herein without departing from the spirit and scope of the present invention. Therefore, the following detailed description is not meant to be limiting.

DETAILED DESCRIPTION

Methods

Methods of making transgenic animals are provided by the present disclosure. The methods allow site-specific integration of a polynucleotide sequence of interest into a genome of the mammal (e.g., a mouse). As such, the site of integration is known and/or predicted before the transgenic animal is made. The methods result in not only an integration of an intact polynucleotide sequence as intended, but also the integration of a known copy number of the sequence. The methods additionally provide robust and ubiquitous expression of the integrated sequence in the resultant transgenic animal in vivo. Further, the transgenic animal can pass the integrated sequence to its progeny without laborious experiments that involve chimeric animals or further selection.

In some embodiments, the methods of the present disclosure involve introducing a circular targeting construct, containing a first unidirectional recombination site (e.g., attB) and a polynucleotide sequence of interest, and a unidirectional recombinase into a cell. The genome of the cell contains a second unidirectional recombination site (e.g., attP). The unidirectional site-specific recombinase introduced into the cell can then facilitate recombination between the first and second unidirectional recombination sites (e.g., between attB and attP). The cell is maintained under conditions that facilitate such a recombination. The result of the recombination between the unidirectional recombination sites is a site-specific integration of the polynucleotide sequence of interest into the genome of the cell. The integrated sequence is then flanked on both sides by hybrid sites (e.g., attR and attL).

For example, one step of a method of the present disclosure is to introduce into a single cell embryo a nucleic acid construct (e.g., a targeting construct), containing a first unidirectional recombination site capable of recombining with a second unidirectional recombination site found within the genome of the mammal from which the cell was derived. The nucleic acid construct further comprises a polynucleotide sequence of interest that is to be inserted. In some embodiments, the cell in which the recombination takes place is a mammalian zygote that is homozygous for the second unidirectional recombination site (e.g., attP recombination sites).

In some embodiments, the methods of present disclosure involve inserting a polynucleotide sequence of interest utilizing a cassette-exchange recombination reaction. In such a reaction, a polynucleotide sequence to be inserted into the genome of a cell is flanked on both sides (e.g., flanked on both the 5' side and on the 3' side) by first unidirectional recombination sites capable of recombining with second unidirectional recombination sites found within the genome of a cell. The cell contains two or more of the second unidirectional recombination sites at a predetermined location (e.g., a predetermined locus, e.g., the R26 locus, described further herein). A unidirectional recombinase facilitates a recombination reaction wherein both of the first unidirectional recombination sites flanking the polynucleotide sequence of interest recombine with corresponding second unidirectional recombination sites within the genome of the target cell, thus facilitating a cassette exchange recombination reaction wherein the polynucleotide sequence of interest (located between the two first unidirectional recombination sites) is inserted into the genome of the cell.

In some embodiments, the methods of the present disclosure optionally provide for removal of at least a portion of the nucleic acid that is inserted into the genome of a cell by a recombination reaction. In such embodiments, the nucleic acid sequence being inserted into the genome of the cell may comprise an additional recombination site located either 3' or 5' to a coding sequence of interest, and the genome of the cell may comprise a corresponding recombination site located either 3' or 5' to the second unidirectional recombination site described above. For example, in some embodiments, following a primary recombination reaction to insert a nucleic acid of interest into the genome of a cell, a secondary recombination reaction is carried out in order to facilitate removal of at least a portion of the nucleic acid sequence that was inserted in the primary recombination reaction (e.g., removal of a bacterial backbone portion of a plasmid). Such secondary recombination reactions can be accomplished, e.g., using either unidirectional or bidirectional recombination sites and recombinases, provided there is no cross-reactivity between the recombination sites and recombinases used in the primary recombination reaction. For example, if a primary recombination reaction uses ϕC31 as the unidirectional recombinase, then a different unidirectional recombinase, such as, e.g., TP901-1 or R4 recombinase may be used to carry out a secondary recombination reaction. In some embodiments, bidirectional recombination sites and recombinases may be used to carry out a secondary recombination reaction. Exemplary bidirectional recombination sites and corresponding bidirectional recombinases are well known in the art, and include, e.g., FRT recombination sites and FLP recombinases, loxP recombination sites and Cre recombinases, and the like.

Recombinases used to practice the methods of the present disclosure may be introduced into a target cell before, concurrently with, or after the introduction of a targeting nucleic acid construct. The recombinase need be present for only a period of time necessary for insertion of the nucleic acid fragments into the genome being modified. There are several ways that a recombinase may be introduced into a cell. The recombinase may be introduced, for example, as a polypeptide, or a nucleic acid (such as RNA or DNA) encoding the recombinase. Where a purified recombinase protein is used, a transient presence of the protein and its function are ensured. The recombinase can be directly introduced into a cell as a protein, for example, using liposomes, coated particles, or microinjection. Alternatively, a gene encoding the recombinase can be included in a nucleic acid (e.g., an expression vector) used to transform the cell. Where the recombinase is introduced in a vector, the expression of the altered recombinase may be regulated, for example, by placing the expression of the recombinase under the control of a regulatable promoter (i.e., a promoter whose expression can be selectively induced or repressed). In one example, the method can involve introducing the recombinase in the form of an mRNA. In such an example, there would then be no requirement for transcription of the recombinase gene and the recombinase gene would be extremely unlikely to become integrated into the genome.

Certain steps of the methods of the present disclosure are presented below as examples of how to prepare a transgenic mammal of the present disclosure. First, mice that are heterozygous or homozygous for a first unidirectional recombination site (e.g., attP) are generated using traditional methods that rely on homologous recombination in mouse ES cells. See examples below. Locations of such first recombinataion sites include Rosa26 (R26) locus on mouse chromosome 6 and/or the intergenic Hipp11 (H11) locus on mouse chromosome 11.

Superovulated females that are heterozygous or homozygous for a first unidirectional recombination site, or that are wild type, may then be crossed to corresponding males to generate heterozygous or homozygous attP-containing zygotes. A nucleic acid construct containing a polynucleotide sequence of interest is then microinjected into a single pronucleus and/or cytoplasm of each zygote. The introduction may be carried out, e.g., by injection into the pronucleus and/or cytoplasm of a fertilized egg before fusion of the male and female pronuclei, or by injection into the nucleus of an embryonic cell (e.g., the nucleus of a two-cell embryo) following the initiation of cell division. Embryos can also be infected with viruses, especially retroviruses, in order to carry out recombination with a nucleic acid sequence of interest. The cell is further treated with a recombinase, or a nucleic acid encoding the recombinases, as described below to promote integration of the nucleic acid sequence of interest into the genome.

Once the nucleic acid construct is injected, recombination can occur in the presence of a recombinase. The polynucleotide sequence of interest is inserted at a site of the genome containing a unidirectional recombination site. In some embodiments, a secondary recombination reaction can then be carried out, e.g., to remove at least a portion of the polynucleotide sequence that was inserted (e.g., to remove bacterial backbone portions of a plasmid). The surviving zygotes are then implanted into the oviducts of pseudo-pregnant recipient mothers. The procedure for generating transgenic rats is similar to that of mice. Rodents suitable for transgenic experiments can be obtained from standard commercial sources such as Charles River (Wilmington, Mass.), Taconic (Germantown, N.Y.), Harlan Sprague Dawley (Indianapolis, Ind.), etc. Methods of manipulating rodent embryos and for microinjection can take on variations of the above-described procedures based on what is known in the art.

Mature mice from such embryos manipulated by the methods of the present disclosure contain an insertion of the polynucleotide sequence of interest in their somatic DNA and germline DNA. The present methods can eliminate procedures that involve targeting ES cells or breeding chimeric mammals that traditional methods require. Further, the present methods promote insertion of the polynucleotide sequence as intact as it is present in the nucleic acid construct. Incidences where there are truncation and/or insertion of multiple copies are greatly reduced. As such, the present methods allow predictability in the location of insertion and the copy of sequence that is inserted. Transgenic mammals carrying the inserted polynucleotide sequence can be identified by methods well known in the art, e.g., by polymerase chain reaction or Southern blotting.

Cells:

Cells suitable to be employed in the methods of the present disclosure in making a transgenic mammal include mammalian cells that contain a recombination sequence (e.g., pseudo-recombination sequence) recognizable by a uni-directional recombinase. The cells used in the microinjection step described above include zygotes that are heterozygous or homozygous for a first recombination site (e.g., attP).

Suitable mammalian cells include those from non-human primates, rodents (such as mice and rats), humans, and the like. Cells that contain one or more genetically engineered sites can also be used in the present methods. Where the cells are derived from a mouse, the cells can contain one or more recombination sites (e.g., attP) at either the Rosa26 (R26) locus on mouse chromosome 6, the intergenic Hipp11 (H11) locus on mouse chromosome 11, or both. In certain cases, the cells lack a promoter (e.g., VASA promoter) that is either genetically engineered or native at or near the location where the recombination site is.

The cell may further contain a uni-directional recombinase as a polypeptide, or its encoding nucleic acid, as noted above. In some embodiments, the cells may contain a bidirectional recombination site and/or a bidirectional recombinase. The cells may contain a bidirectional recombinase as a polypeptide or its encoding nucleic acid, as noted above.

Recombinases:

Recombinases that may be used to incorporate a polynucleotide sequence into the genomes of a cell include those that carry out uni-directional, site-specific integration. Examples are phage recombinases such as ϕC31, TP901-1, and R4, wild-type or variations thereof. Other recombinases that may be used are described in US Pat. Pub. No. 20100190178, disclosure of which is incorporated by reference. Sequences encoding recombinases useful in the method of the present disclosure known in the art and are disclosed therein.

In some embodiments, bidirectional recombinases may be used to carry out a secondary recombination reaction. Exemplary bidirectional recombinases include Cre recombinase and FLP recombinase. Other bidirectional recombinases known in the art may also be used.

Recombinases and their encoding nucleic acids can be produced recombinantly or purified as known in the art. Where the recombinases are provided as polypeptides, the polypeptides having the desired recombinase activity can be purified to a desired degree of purity by methods known in the art of protein purification, including, but not limited to, ammonium sulfate precipitation, size fractionation, affinity chromatography, HPLC, ion exchange chromatography, heparin agarose affinity chromatography.

Recombination Sites:

Recombination sites used in the present methods include those recognized by uni-directional, site-directed recombinases, such as ϕC31, TP901-1, and R4, wild-type or variations thereof. Any sites recognized by recombinases described in US Pat. No. 20100190178 may also be used.

Binding sites for phage integrase enzymes as recombinases, such as the ϕC31 integrase, are traditionally called attB and attP (i.e., the target sites of the integrase). These sites have a minimal length of approximately 34-40 base pairs (bp) (Groth, A. C., et al., Proc. Natl. Acad. Sci. USA 97, 5995-6000 (2000)). These sites are typically arranged as follows: AttB comprises a first DNA sequence attB5', a core region, and a second DNA sequence attB3' in the relative order attB5'-core region-attB3'. AttP contains a first DNA sequence (attP5'), a core region, and a second DNA sequence (attP3') in the relative order attP5'-core region-attP3'. The recombinase mediates production of recombination-product sites that can no longer act as substrates for the recombinase. The recombination-product sites contain, for example, the relative order attB5'-recombination-product site-attP3' and attP5'-recombination-product site-attB3'. Where the recombination sites are recognized by φC31 or its variants, the sites can be variants of the native attP/attB sequences, such as tandem repeats (e.g., three repeats such as attPx3), truncated sequences, or both. Some variants may differ in one or more nucleotide sequences and can be naturally-occurring or man-made. Some variations of the recombination sites are referred to as pseudo-site sequences. Any of these sequences can be used as a first recombination site, a second recombination site or both, for genomic integration and stable expression of introduced DNA.

Some examples include: (a) a recombination site (attB) in the targeting nucleic acid construct and a pseudo phage genomic recombination site (pseudo-attP); or conversely, (b) a pseudo-attB site and an attP site; or alternatively, (c) a pseudo-attB site and a pseudo-attP site. As noted above, one or more these sites can be naturally-occurring or pseudo-sequences that are inserted into the construct and/or the mammal to be made transgenic.

Recombination sites used in the methods of the present disclosure may also include, e.g., bidirectional recombination sites, such FRT recombination sites or loxP recombination sites.

Where the transgenic mammal to be made by the present methods is a mouse, one or more copies of the recombination sites that are employed by the subject methods may be located at either the Rosa26 (R26) locus on mouse chromosome 6, the intergenic Hipp11 (H11) locus on mouse chromosome 11, or both. In certain cases, the recombination sites do not contain a promoter sequence and/or an enhancer sequence in a cassette that is not related to the expression of the polynucleotide sequence to be inserted. In other words, prior to the recombination event carried out by the present methods, the genome of the animal does not contain any promoter, enhancer, or promoter-enhancer sequences at or near the second recombination site. As seen in the examples below, certain mice made by the present methods do not contain the NVφ (or VASA) cassette at the recombination site (e.g., the Rosa26 (R26) locus on mouse chromosome 6 or the intergenic Hipp11 (H11) locus on mouse chromosome 11).

After a recombination event mediated by a unidirectional site-specific recombinase (e.g., φC31), the post-recombination recombination sites are no longer able to act as substrate for the φC31 recombinase. This uni-directional nature results in stable integration with little or no recombinase mediated excision.

Targeting Constructs:

Constructs are also provided herein for site-specific integration of a polynucleotide sequence into the genome of a mammal. In some embodiments, the vector is (i) circular and contains (ii) a polynucleotide of interest operably linked to a promoter, and (iii) a first unidirectional recombination site, in which the genome of the cell contains a second unidirectional recombination site. Recombination between the first and second unidirectional recombination sites in the presence of a unidirectional recombinase results in intact site-specific integration of the polynucleotide of interest.

In some embodiments, targeting constructs of the present disclosure may contain multiple copies a first unidirectional recombination site. For example, in some embodiments, a polynucleotide sequence of interest may be flanked by copies of a first unidirectional recombination site (e.g., a copy of the first unidirectional recombination site may be located adjacent to the polynucleotide sequence of interest in the 5' direction as well as the 3' direction).

In some embodiments, targeting constructs may comprise a secondary recombination site, typically located 3' to a polynucleotide sequence of interest. Such secondary recombination sites may be, e.g., unidirectional or bidirectional recombination sites, and may be used, e.g., to facilitate excision of at least a portion of a nucleic acid sequence that is inserted into the genome of a cell during a primary recombination reaction.

In addition, targeting constructs of the present disclosure may contain nucleic acid fragments such as control sequences, marker sequences, selection sequences and the like as discussed below. In some embodiments, constructs may be a circular minicircle DNA that lacks a plasmid backbone (e.g., bacterial plasmid backbone). In certain cases, the targeting construct may contain no more than 3, no more than 2, no more than 1, or no other elements aside from an enhancer (e.g., cytomegalovirus enhancer), a promoter (e.g., β-actin promoter), a recombination site, one or more polynucleotide sequences to be inserted, and a poly-A signal. Where the construct contains more than one distinct polynucleotide sequence to be inserted, each sequence may be flanked by an enhancer, a promoter, a poly-A tail, and/or other elements necessary for the expression of the sequence in vivo. The intervening sequences between any two adjacent elements of a nucleic acid construct may be no more than about 2000 bp, no more than about 1000 bp, no more than about 500 bp, no more than about 300 bp, or no more than about 100 bp or less.

Where the targeting construct contains one or more additional elements aside from a promoter or a promoter-enhancer sequence, the construct may contain other useful components, such as a bacterial origin of replication and/or a selectable marker, an inducible element sequence, an epitope-tag sequence, and the like, discussed below.

Promoter and promoter-enhancer sequences are DNA sequences to which RNA polymerase binds and initiates transcription. The promoter determines the polarity of the transcript by specifying which DNA strand will be transcribed. Eukaryotic promoters are complex arrangements of sequences that are utilized by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g., AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV).

Promoters may be, furthermore, either constitutive or regulatable. Inducible elements are DNA sequence elements which act in conjunction with promoters and may bind either repressors or inducers. In such cases, transcription is virtually "shut off" until the promoter is derepressed or induced, at which point transcription is "turned-on."

Examples of eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gal1 gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline responsive promoter, and the like.

Selection markers are valuable elements in expression vectors as they provide a means to select for growth of only those cells that contain a vector. Such markers are typically of two types: drug resistance and auxotrophic. A drug resistance marker enables cells to detoxify an exogenously added drug that would otherwise kill the cell.

Common selectable marker genes include those for resistance to antibiotics such as ampicillin, tetracycline, kanamycin, bleomycin, streptomycin, hygromycin, neomycin, Zeocin™, G418, and the like.

A further element useful in an expression vector is an origin of replication. Replication origins are unique DNA segments that contain multiple short repeated sequences that are recognized by multimeric origin-binding proteins and that play a key role in assembling DNA replication enzymes at the origin site. Suitable origins of replication for use in expression vectors employed herein include *E. coli* oriC, colE1 plasmid origin, SV40, and EBV oriP (useful in mammalian systems), and the like.

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr, chitin binding domain, and the like.

A further useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The foregoing elements can be combined to produce expression vectors suitable for use in the methods of the present disclosure. Those of skill in the art would be able to select and combine the elements suitable for use in their particular system in view of the present disclosure.

Suitable eukaryotic plasmids from which on can construct the nucleic acid vector employed in the present disclosure are well known in the art. See, for example, Botstein et al., Miami Wntr. SyTnp. 19:265-274, 1982; Broach, In: "The Molecular Biology of the Yeast *Saccharomyces*: Life Cycle and Inheritance", Cold Spring Harbor Laboratory, Cold Spring Harbor, N.Y., p. 445-470, 1981; Broach, Cell 28:203-204, 1982; Dilon et al., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980.

The targeting cassettes described herein can be constructed utilizing methodologies known in the art of molecular biology (see, for example, Ausubel or Maniatis) in view of the present disclosure. As described above, the targeting constructs are assembled by linking a recombination site, polynucleotides encoding sequences of interest operably linked to a promoter of interest; and, optionally other elements described above, into a circular nucleic acid.

One method of obtaining polynucleotides, including suitable regulatory sequences (e.g., promoters) is PCR. General procedures for PCR are taught in MacPherson et al., PCR: A Practical Approach, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. After amplification, the resulting fragments can be detected by agarose gel electrophoresis followed by visualization with ethidium bromide staining and ultraviolet illumination. See examples below.

Transgenic Non-Human Animals

The present disclosure provides non-human transgenic animals whose genomes have been modified by employing the methods and compositions provided herein. Transgenic animals (e.g., transgenic mice) may be produced employing the methods of the present invention to serve as a model system for the study of various disorders and for screening of drugs that modulate such disorders.

A "transgenic" animal refers to a genetically engineered animal, or offspring of genetically engineered animals. A transgenic animal usually contains material from at least one unrelated organism, such as, from a virus. The term "animal" as used in the context of transgenic organisms means all species except human. It also includes an individual animal in all stages of development, including embryonic and fetal stages. Rodents, such as mice and rats, are contemplated. Where the transgenic animal is a mouse, the genome of the transgenic mouse contains a first recombination site at the Rosa26 (R26) locus on mouse chromosome 6 or the intergenic Hipp11 (H11) locus on mouse chromosome 11. The mouse of the present disclosure is homozygous for the first recombination site. See examples below for detail.

The transgenic animal of the present disclosure also include those that contain a nucleic acid fragment of interest that is stably integrated into both its somatic DNA and also its germ line DNA of a mature animal. For example, a transgenic mouse can be homozygous for the integrated sequence at the Rosa26 (R26) locus on mouse chromosome 6 and/or the intergenic Hipp11 (H11) locus on mouse chromosome 11. The nucleic acid of interest that has been integrated then can be inherited in normal Mendelian fashion. The nucleic acid fragment of interest can be any one polynucleotide. Examples include those that encode proteins or RNA, whose function can be subject to investigation as they are expressed in a live animal. The exogenous product that is encoded by the inserted polynucleotide can also be used to disrupt and/or interfere with expression of an endogenously produced protein of interest, yielding transgenic animals with decreased expression of the protein of interest. Alternatively, the encoded product may be a reporter, such as a luminescent or fluorescent protein, whose activity and/or presence can be assessed to further investigations in biological research.

The transgenic animal of the present disclosure, such as a transgenic mouse, also can be described as a germ cell line transgenic animal. For example, a "germ cell line transgenic mouse" is a transgenic mouse in which the genetic information provided by the present method has been taken up and incorporated into a germ line cell, therefore conferring the ability to transfer the information to offspring. If such offspring, in fact, possess some or all of that information, then they, too, are transgenic animals.

Where the inserted polynucleotide sequence is expected to be expressed ubiquitously, the transgenic mammal of the present disclosure exhibits ubiquitous expression of the inserted polynucleotide sequence in more than about 60%, more than about 70%, more than about 80%, more than about 85%, more than about 90%, more than about 95%, more than about 99% of the tissues. Where the inserted polynucleotide sequence is expressed in more than one type of tissue, the expression levels of the polynucleotide sequence in tissues of the transgenic mammal are about the same (e.g., not significantly different). The expression levels among different tissue types may differ by about 30%, about 20%, about 15%, about 10%, about 5%, about 1% or less.

Kits

Kits for the making of a transgenic mammal (e.g., mouse) are also provided. The cells, mouse cells or zygotes homozygous for a recombination site, expression cassettes, targeting constructs, vectors, recombinases, and/or recombinase-coding sequences (e.g., mRNA) of the present disclosure can be formulated into kits. Components of such kits can include, but are not limited to, containers, instructions, solutions, buffers, disposables, and hardware.

Kits will typically comprise one or more nucleic acid constructs with instructional materials disclosing means of use these constructs in the procedures of building a nucleic acid minicircle to be employed in the present methods. The kits may also include additional components to facilitate the particular application for which the kit is designed (e.g., positive controls, negative controls, and/or reporter expression in vivo). The kits may additionally include buffers and other reagents routinely used for molecular biology, microinjection, and assessment by PCR, etc. Such kits and appropriate contents are well known to those of skill in the art.

The kits can optionally include instructional materials for the use of a mouse homozygous for a recombination site at either the Rosa26 (R26) locus on mouse chromosome 6, the intergenic Hipp11 (H11) locus on mouse chromosome 11, or both.

The invention will now be described in greater detail by reference to the following non-limiting Examples.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

EXAMPLES

The following examples are offered to illustrate, but not to limit, any embodiments provided by the present disclosure. The following methods and materials were used throughout the examples provided below.

Methods and Materials

Recombinant DNA:

Standard methods of recombinant DNA manipulation were used to construct all plasmids used in this study. All PCR for DNA construction was done with Phusion DNA polymerase (Finnzymes, Finland). All DNA fragments that were amplified by PCR were fully sequenced after cloning.

pBT296 (pBS-U-attP-FRT5-pSV40-Neo-pA-FRT5):
The following were subcloned into a modified pBluescript:
1) a unique sequence "U" from the promoter of yeast his3 gene: (GGTGATAGGTGGCAAGTGGTATTCCGTAAGGATATC) (SEQ ID NO:1);
2) the single "full-length" attP site from pTA-attP (Groth A C et al. (2000) *Proc Natl Acad Sci USA* 97:5995).
3) FRT5 (GAAGTTCCTATTCCGAAGTTCCTATTCTTCAAAAGGTATAGGAACTTC) (SEQ ID NO:2) (Seibler et al. (1998) *Biochemistry* 37:6229)-flanked neomycin resistance gene driven by an SV40 promoter.

pBT298 (pBS-U-attPx3-FRT5-pSV40-Neo-pA-FRT5):
Similar to pBT296 set forth above, except that the single attP site was replaced by three sequential attP sites (70 bp each, sequence of a single site: CGGGAGTAGTGCCCCAACTGGGGTAACCTTTGAGTTCTCTCAGTTGGGGGCG TAGGGTCG) (SEQ ID NO:3) synthesized by Celtek Genes (Nashville, Tenn.).

pBT305 (pBS-U-attPx3-FRT5-pSV40-Neo-pA-PL-FRT5):
PL represents a polylinker SbfI-HpaI-AatII. The plasmid was generated by inserting annealed oligos: PR402 (ctagCCTGCAGGaattaaGTTAACaattaaGACGTC) (SEQ ID NO:4) and PR403 (ctagGACGTCttaattGTTAACttaattCCTGCAGG) (SEQ ID NO:5) into the XbaI site of pBT298 and thereby destroying the XbaI sites on both ends of the PL.

pBT307 (pBS-U-attPx3-FRT5-pSV40-Neo-pA-φC31o-pA-FRT5):
φC31o was amplified by PCR from pPGKFC31obpA (Raymond et al. (2007) PLoS ONE 2:e162 and subloned into pBT305.

pBT308b (pTOPO-pVasa):
A previously described fragment of the VASA promoter (Gallardo et al. (2007) Genesis 45:413) was amplified by PCR from genomic DNA of the FVB strain and cloned into pTOPO.

pBT309a (pBS-U-attPx3-FRT5-pSV40-Neo-pA-pVasa-φC31o-pA-FRT5):
pVasa was subcloned from pBT308b (pTOPO-pVasa) into pBT307.

pBT310 (pBS-U-attP-FRT5-pSV40-Neo-pA-pVasa-φC31o-pA-FRT5):
NheI/AscI fragment from pBT309a was subcloned into NheI/AscI digested pBT296.

pBT311 (pH11-U-attPx3-FRT5-pSV40-Neo-pA-pVasa-φC31o-pA-FRT5):
Generated from PmeI/AscI-digested pHIPP11 and SwaI/AscI-digested pBT309a.

pBT312 (pH11-U-attP-FRT5-pSV40-Neo-pA-pVasa-φC31o-pA-FRT5):
Generated from PmeI/AscI-digested pHIPP11 and SwaI/AscI-digested pBT310.

pBT313 (pR26-U-attPx3-FRT5-pSV40-Neo-pA-pVasa-φC31o-pA-FRT5):
SwaI/AscI-digested insert from pBT309a was subcloned into SwaI/AscI-digested
pROSA26 (Srinivas et al. (2001) *BMC Dev Biol* 1:4).

pBT314 (pR26-U-attP-FRT5-pSV40-Neo-pA-pVasa-φC31o-pA-FRT5):
SwaI/AscI-digested insert from pBT310 was subcloned into SwaI/AscI-digested pROSA26 (Srinivas et al. (2001) *BMC Dev Biol* 1:4).

pBT316 (pattB-pCA-GFP):
"Full-length" attB site was cloned from pTA-attB as SalI fragment into the SalI site of pBT255 (pCA-GFP4m-pA).

pBT317 (pET φC31opA): φC31o gene was amplified by PCR from pPGKφC31obpA using primers PR437 (AACCAACCttaaCCGCCACCATGGATACCTAC) (SEQ ID NO:6) and PR438 (AATAggatccTTTTTTTTTTTTTTT TTTTTTTTTTTTTTTTctcgagTCACACTTTCCGCTTTT TCTTAGG). (SEQ ID NO:7) The PCR was digested with BamHI and MseI and cloned into BamHI/NdeI-digested pET11φC31pA (Hollis et al. (2003) *Reprod Biol. Endocrinol* 1:79).

pBT340 (pattB-pCA-GFP-pA-FRT5-pPGK-Flpo-pA). A fragment containing FRT5-pPGK-FlpopA was PCR amplified from pPGKFLPobpA (Addgene plasmid 13793) (Ref. 4) and cloned between NotI and AscI sites of pBT316.

pBT344 (pattB-pCA-GFP-pA-FRT5—for cloning any DNA fragment to be integrated as a full plasmid using φC31; the bacterial backbone can be subsequently removed by crossing to GFP-Flpo mice): The pPGK-Flpo-pA portion was removed from pBT340.

pBT346 (pλ-attB-pCA-GFP): I-SceI restriction site and the λattL1 were amplified from pENTR-TopoD using PR493 (aaagaGGTACCagttacgctagggataacagggtaatatagCAAATAA TGATTTTATTTTGACTG ATAG) (SEQ ID NO:8) and PR494 (aaataCTCGAGagcctGCTTTTTTGTACAAAG TTG) (SEQ ID NO:9). The PCR product was digested with Acc651 and XhoI and inserted into the Acc65I/XhoI-digested pBT316. Subsequently, the λ attR1 site was amplified from pENTR-TopoD using PR495 (aagaaGCGGCCGCacaagttttg-tacaaaaaagcTGAACG) (SEQ ID NO:10) and PR496 (AA-GAAGagctcCATAGTGACTGGATATGTTGTGTTTTA) (SEQ ID NO:11) and cloned into the SacI/NotI-digested construction intermediate to generate pBT346.

pBT366 (pattB-Hb9-GFP-pA-FRT5). The filled-in Hb9-GFP XhoI fragment from pHB9-EGFP (Addgene plasmid 16275) (Ref. 9) was subcloned into the PacI/AscI digested and filled-in pBT344.

pBT374 (pattB-pCA-GFP-pA-attBSwa): The filled-in SalI fragment containing the attB site from pBT316 was subcloned into the SwaI site of pBT316. This plasmid was used for initial cassette exchange tests, but for future use pBT378 (below) is recommended, as it contains more convenient restriction sites.

pBT378 (pattB-pCA-GFP-pA-attB—for φC31-mediated cassette exchange): It contains more convenient restriction sites than pBT374 that enable replacement of the pCA-GFP-pA insert with an insert of choice (ClaI, HindIII, PacI, PmeI, PstI between the first attB and pCA, and SwaI, AscI, SpeI and NotI between the pA and the second attB). It was created by subcloning the filled in SalI fragment containing the attB site from pBT316 into the BstXI-linearized and filled-in pBT316.

Gene Targeting in Mouse ES Cells:

Standard techniques were used to modify R1 mouse ES cells (Nagy et al. (1993) Proc Natl Acad Sci USA 90:8424). Individual G418-resistant clones were evaluated for homologous recombination by long-range PCR, using LA Taq (Takara Bio) and the following primers for H11 5' arm: PR374 (atgtgaggcaggagatgagagaggaatgactggtcac) (SEQ ID NO:12) and PR432 (GATATCCTTACGGAATACCACT-TGCCACCTATCACC) (SEQ ID NO:13); H11 3' arm: PR351 (aataaGCTAGCctcgagGATATCctgtgccttctagttgccag) (SEQ ID NO:14) and PR422 (ccattttttagtaccccctctacactcctcc) (SEQ ID NO:15); R26 5' arm: Rosa3 (ccactgaccgcacggg-gattc) (SEQ ID NO:16) and PR432 (see above), and R26 3' arm: PR351 (see above) and PR395 (gttgagggcaatctgg-gaaggt) (SEQ ID NO:17).

The clones containing correctly recombined targeting vectors were used to generate mouse chimeras by injection into C57BL/6J blastocysts. The chimeras were crossed to B6D2 F1 females (F1 females from a cross between C57BL/6J and DBA2/J mice; Stock#100006, Jackson Lab). Agouti progeny were genotyped for the presence of the knockin allele using the following primers for H11: (PCR1+2 in FIG. 1): SH176 (tggaggaggacaaactggtcac) (SEQ ID NO:18), SH178 (ttc-cctttctgcttcatcttgc) (SEQ ID NO:19) and PR432 (see above). The expected sizes are: 147 bp for the knockin and 321 bp for wt. For R26 the primers used were: Rosa10 (CTCTGCTGC-CTCCTGGCTTCT) (SEQ ID NO:20), Rosa11 (cgaggcggat-cacaagcaata) (SEQ ID NO:21), and PR432 (see above). Expected sizes are: 168 bp for the knockin and 330 bp for wild-type.

After electroporation of targeting constructs pBT311, pBT312, pBT313, and pBT314 into mouse ES cells of 129 strain origin, individual G418-resistant clones were evaluated for homologous recombination by long-range PCR (see above). The clones containing correctly recombined targeting vectors were used to generate mouse chimeras by injection into C57BL/6 blastocysts. The chimeras were crossed to B6D2 μl females (F1 females from a cross between C57BL/6J and DBA2/J mice; Stock No. 100006, Jackson Lab). Agouti F1 progeny were genotyped for the presence of approproate knockin allele using the same long-range PCRs that were used for screening ES cells. Subsequent genotyping was performed with short-range PCR described above.

Mouse Maintenance and Breeding:

All experimental procedures were carried out in accordance with the APLAC (Administrative Panel on Laboratory Animal Care) protocol and the institutional guidelines by the Veterinary Service Center (VSC) at Stanford University.

The F1 attP-knockin animals obtained from the cross of chimeras to B6D2 F1 females were crossed to each other to establish homozygous knockin mouse lines. These lines were maintained by intercrosses between homozygous animals. To outcross the mice to FVB (Charles River), a homozygous male and his transgenic male progeny were crossed to FVB females, for a total of 4 generations. During the outcrossing, transgenic mice of white coat color were preferentially selected. The $4^{th}$ generation outcrossed mice were crossed to each other to make homozygous males and females that would be subsequently used to produce zygotes for microinjection. The FVB N4 homozygous line was subsequently maintained by homozygous crosses. For testing transgenic founders F0 animals were crossed to wild-type CD1 mice (Charles River). For F2 and F3 generation, crossing to CD1 was continued.

Preparation of DNA and mRNA for Microinjection:

Plasmid DNA was prepared using Qiagen mini-preps and was subsequently extracted twice with a phenol:chloroform (50:50) mix and twice with chloroform only. The DNA was precipitated with 1/10 volume of 3M sodium-acetate pH 5.2 and 2.7 volumes of ethanol, and subsequently dissolved in microinjection TE buffer (miTE; 0.1 mM EDTA, 10 mM Tris pH 7.5). The DNA was filtered through a sterile 0.2 μm filter and the concentration was determined using Nanodrop spectrophotometer (Thermo Scientific). The DNA was diluted to 6 ng/μl by sterile miTE and was kept at −80° C. until the injection. The DNA was tested to be RNase-free by incubation with an in vitro transcribed RNA at 37° C. for 1 h and then by running the mix on a 1% agarose gel. Prior to loading on the gel, the RNA was denatured as described below for the analysis of in vitro transcribed RNA.

Capped mRNA for φC31o and Flpo was generated using mMESSAGEmMACHINE in vitro transcription kit from Ambion according to the manufacturer's instructions from pBT317 and pFlpo, respectively. The integrity of the RNA was assessed by electrophoresis on a 1% agarose gel. Prior to loading on the gel, the RNA was denatured using the loading buffer provided in the Ambion kit according to the manufacturer's instructions.

Microinjection for Generation of Site-Specific Integrants:

Microinjection was performed with an established setup at the Stanford Transgenic Facility. Superovulated homozygous attP-containing females were crossed to corresponding males to generate homozygous attP-containing zygotes. A DNA/mRNA mix of interest was microinjected into a single pronucleus and cytoplasm of each zygote using a continuous flow injection mode. The surviving zygotes were implanted into oviducts of pseudo-pregnant CD1 (Charles River) recipient mothers. All injection mixes contained 3 ng/µl DNA and 48 ng/µl of in vitro transcribed φC31o mRNA in microinjection TE buffer (miTE; 0.1 mM EDTA, 10 mM Tris pH 7.5). The injection mixes were prepared fresh before each injection by mixing the equal volumes of 6 ng/µl DNA solution and 96 ng/µl mRNA solution.

Qiagen maxi-prep DNA that was filtered through the 0.2 µm filter has been tested for injections. It was noticed that although this DNA was RNase-free, it was more difficult to inject. Phenol/chloroform extractions followed by filtration as described above greatly facilitated the injection of this DNA. Use of homozygous attP-containing F0 animals that do not contain site-specific integrations and were obtained from injections in subsequent injections are not recommended, as they may contain random insertions or conversions of attPx3 into attPx2 or a single attP, which, although infrequent, have been observed. The use of these animals for subsequent injections is recommended only after proper control PCRs exclude the animals with undesirable events mentioned above.

To test for integrity of RNA after each injection, the remaining DNA/RNA injection mix was analyzed on 1% agarose gel (after incubation with the Ambion loading buffer as described for the analysis of in vitro transcribed RNA).

Figure 1:
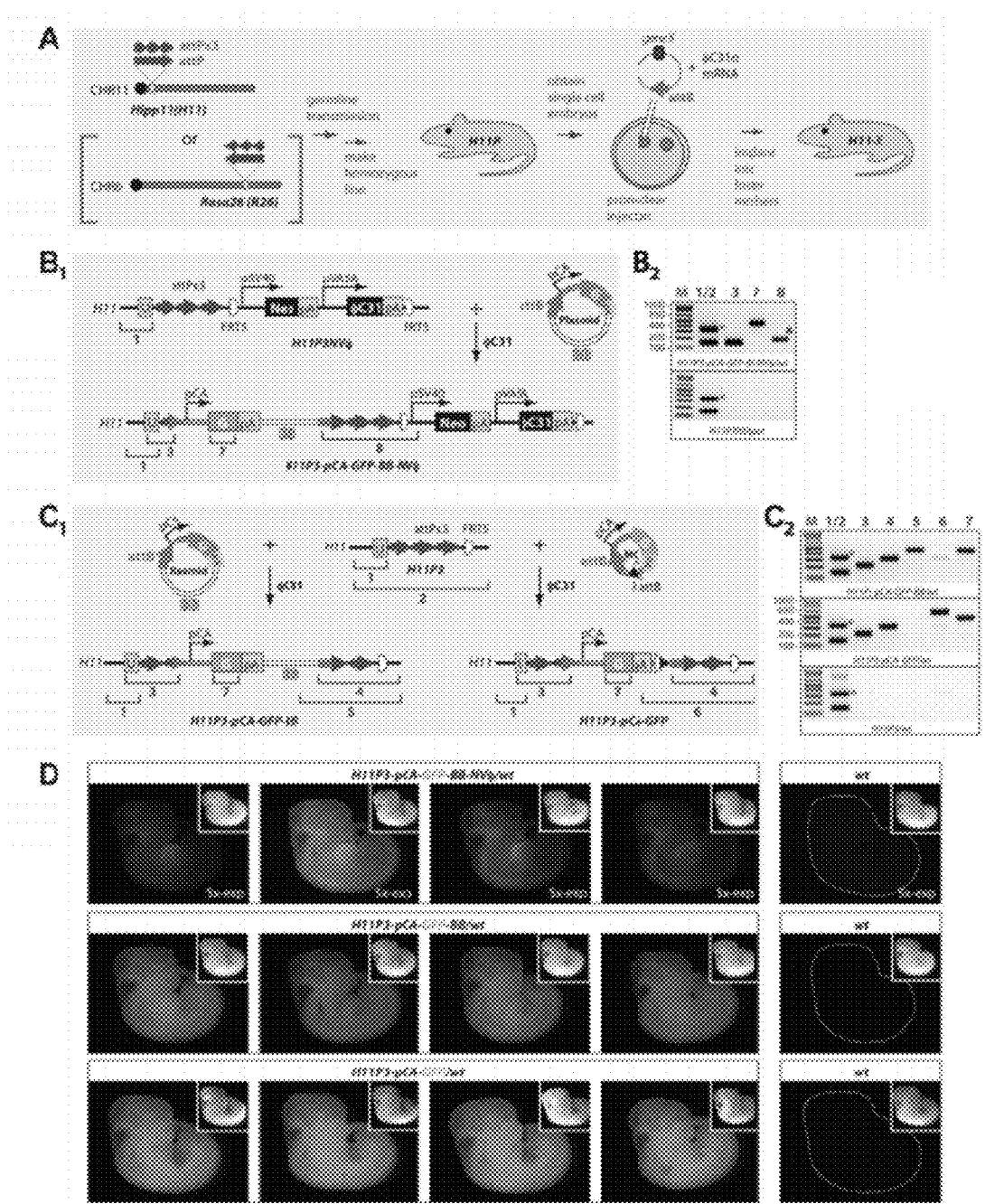
FIG. 1. Site-specific ϕC31 integrase-mediated transgenesis via pronuclear injection in mice. (Panel A) Overall scheme of the transgenesis process. (Panel $B_1$) Schematic of the recipient H11P3NVϕ locus and the modified H11P3-pCA-GFP-BB-NVϕ locus obtained by ϕC31-catalyzed site-specific insertion of the attB-pCA-GFP plasmid into the second attP site. All three attP sites are suitable recipients for the transgene and the site used in any particular case can be determined by PCR. (Panel $B_2$) PCR results confirming site-specific integration. The DNA template for each PCR panel was obtained from the mice of the genotype designated below each gel. The numbers above correspond to the PCR products designated on the schemes by red brackets and numbers in $B_1$. The primer set #8 amplified a band smaller than expected due to the deletion of two attP sites during integration (spade). The wt H11 locus is also amplified by primer set #2 (asterisk, see panel $C_1$). (Panel $C_1$) Schematic of the recipient H11P3 locus, obtained by Flpo-mediated removal of the NVϕ cassette, and the two products obtained by ϕC31-catalyzed site-specific insertion of the attB-pCA-GFP plasmid (left branch)

Microinjection of Flpo mRNA for Generation of Flp-Out Alleles:

To remove the VASA cassette, which is flanked by FRT5 sites, the capped in vitro transcribed Flpo mRNA obtained from pFlpo was injected into the cytoplasm of attP-homozygous embryos. Microinjection was performed as described in the section above. The average efficiency of Flp-out was 25.6% (32 out of 125) for H11P(3)NVφ and 7.4% (6 out of 81) for R26P(3)NVφ. None of the animals obtained were homozygous Flp-outs (n=206) based on the PCR that can detect both the Flp-out and non-Flp-out alleles (FIG. 1). The animals containing the same Flp-out allele were mated to each other to create homozygous Flp-out mouse lines.

PCR: To test if F1 animals from any particular founder contained both a site-specific insertion and a random insertion, three PCRs on the progeny were carried out:

(PCR3 in FIG. 1): PR425 (ggtgataggtggcaagtggtattc) (SEQ ID NO:22) and PR436 (atcaactaccgccacctcgac) (SEQ ID NO:23). Expected sizes are: 147 bp, 217 bp, 287 bp, and 244 bp, for insertion into the first attP; second attP, third attP, or full-length attP, respectively.

(PCR4 in FIG. 1, for H11P(3) alleles): PR522 (CGATGTAGGTCACGGTCTCG) (SEQ ID NO:24) and PR387 (gtgggactgcttttttccaga) (SEQ ID NO:25). Expected sizes are: 371 bp, 301 bp, 231 bp, and 313 bp, for insertion into the first attP; second attP, third attP, or full-length attP, respectively.

(PCR8 in FIG. 1, for H11P3NVφalleles): PR522 (see above) and PR428 (ccgaaaagtgccacctgaataat) (SEQ ID NO:26). Expected sizes are: 178 bp, 248 bp, 318 bp, for insertion into the first attP; second attP, third attP, respectively.

(PCR7 in FIG. 1): FACS G5' (CTTCAAGTCCGCCATGCCCGA) (SEQ ID NO:27) and GFP2-Hermie (TCCAGCAGGACCATGTGATCGC) (SEQ ID NO:28). Expected size: 420 bp.

100% correlation between GFP-specific and site-specific integration PCR on F1 animals suggested that the corresponding F0 founder most likely contained only a single site-specific insertion. This conclusion was reinforced by quantitative PCR (see below) for GFP to show that a selected number of F1 animals indeed had a single-copy transgene.

In most of the cases (20 out of 28 founders), φC31 catalyzed precise recombination between attP and attB. In 6 cases, integration appeared to occur at two different attP sites, or it caused the deletion of one or more attP sites (for example, see FIG. 2, panel B). These imprecise events occurred only when transgenesis was performed in animals with three tandem attP sites.

To show that a particular insertion into H11P originated from either a plasmid or a minicircle, the following PCRs were performed:

(PCR5 in FIG. 1): PR21 (ctgcaaggcgattaagttgg) (SEQ ID NO:29) and PR387 (gtgggactgcttttttccaga) (SEQ ID NO:30). Expected sizes are 498 bp, 428 bp, 358 bp, and 440 bp, for insertion into the first attP; second attP, third attP, or full-length attP, respectively.

(PCR6 in FIG. 1): PR487 (TCCCCCTGAACCTGAAACAT) (SEQ ID NO:31) and PR387 (see above). Expected sizes are 612 bp, 542 bp, 472 bp, and 554 bp, for insertion into the first attP; second attP, third attP, or full-length attP, respectively.

Tissue Preparation and Immunohistochemistry:

Tissues were obtained from postnatal day 21 (±2 days) mice that were transcardially perfused with 4% paraformaldehyde (PFA) in phosphate buffered saline (PBS). The tissues were post-fixed overnight in 4% PFA, washed once with PBS and then cryoprotected in 30% sucrose overnight. The tissues were embedded in OCT (Tissue-Tek) and stored at −80° C. before cryosectioning. All tissue sectioning was performed using a Leica cryostat. The livers and hearts were sectioned coronally to obtain 10 µm-thick sections, washed in PBS, stained with DAPI and mounted with Fluorogel (Electron Microscopy Sciences, Cat. No. 17985-11). The livers and hearts were imaged with a fluorescence microscope (Nikon). The brains were sectioned sagittally to obtain 30 µm-thick sections, the sections were washed 3 times in PBS and incubated overnight at 4° C. with chicken anti-GFP antibody (Ayes Labs) at 1:500 dilution and monoclonal mouse anti-calbindin antibody (Sigma) at 1:3000 dilution. Following incubation with fluorophore-conjugated secondary antibodies (Jackson ImmunoResearch) and DAPI, the slides were washed 3 times in PBS, mounted in Fluorogel, and imaged with a Zeiss confocal microscope.

E11 embryos were dissected in ice-cold PBS, fixed for 2 h at 4° C. with shaking, washed 3 times in ice-cold PBS, and cryoprotected in 30% sucrose overnight. Embryos were embedded into OCT coronally and sectioned at 12 µm thickness with a Leica cryostat. The sections were washed 3 times in PBS and incubated overnight at 4° C. with chicken anti-GFP antibody (Ayes Labs) at 1:500 dilution and polyclonal rabbit anti-N-terminal Hb9 antibody (generous gift of S. Arber) at 1:1000 dilution. Following incubation with fluorophore-conjugated secondary antibodies (Jackson ImmunoResearch) and DAPI, the slides were washed 3 times in PBS, mounted in Fluorogel, and imaged with a Zeiss confocal microscope.

Quantification of GFP Fluorescence in Tissue Sections:

At least 3 individual images were taken from randomly chosen 10 μm-sections for each liver, by a camera connected to a fluorescence microscope (Nikon) with a 20× objective. The regions of interest were consistently chosen to contain minimal number of large blood vessels, so that the majority of every image would be covered by hepatocytes. All images were taken with the same exposure time (5 ms), same gain and during two continuous days of imaging. At this condition, even the samples with brightest fluorescence had no saturated pixels. Total fluorescence for each image was calculated using ImageJ. Total fluorescence from all images of the same liver was averaged and plotted on the graph in FIG. 4.

Quantitative PCR:

Quantitative PCR was performed as previously described. Each sample was tested in triplicate both for GFP and for the internal control. The primers used for GFP were: LL84 (AAGTCGTGCTGCTTCATGTG) (SEQ ID NO: 32), and LL85 (ACGTAAACGGCCACAAGTT) (SEQ ID NO: 33), and they generate a product of 187 bp. The internal control primers were: IMR0015 (CAAATGTTGCTTGTCTGGTG) (SEQ ID NO: 34) and IMR0016 (GTCAGTCGAGTGCACAGTTT) (SEQ ID NO: 35), and they generate a product of 200 bp.

Animal and Reagent Availability:

Plasmids (containing attB sites or integrase cDNA) and H11P3 and R26P3 homozygous frozen embryos and mice will be distributed through Applied StemCell, Inc. (www.appliedstemcell.com), for prices comparable to those of other distributors (e.g., Addgene for plasmids, Jackson Labs for mice). Applied StemCell also provides services for making customized, integrase-mediated site-specific transgenic mice.

Preparation of Plasmid DNA by a Modified Qiagen Mini-Prep Procedure.

4 ml of DH5α bacterial culture grown in LB broth for not more than 10 h at 37° C. was the starting point. The bacteria were collected in 2 ml tubes by spinning 2 ml of culture twice in the same tube. The recommended volumes of P1, P2 and N3 (Qiagen) were doubled. After loading the samples onto the Qiagen mini-prep columns, the columns were washed twice with buffer PB and then twice with buffer PE (Qiagen). The PB washes diminish but do not abolish RNase contamination. The DNA was eluted in 3-fold diluted EB (Qiagen). The plasmid DNA yield from a single prep was usually in the range of 7.5 to 25 μg. To obtain more DNA, several preps can be performed at the same time and pooled. The concentration was determined using the Nanodrop spectrophotometer (Thermo Scientific) and used at least 5-20 μg in 200 μl of solution for subsequent extractions to remove residual RNase (see below).

Phenol/Chloroform Extraction of Plasmid DNA.

At least 5 μg of DNA in 200 μl of solution were extracted twice with a phenol:chloroform (50:50) mix and twice with chloroform only. The DNA was mixed with 1/10 volume of 3M sodium-acetate pH 5.2, precipitated with 2.7 volumes of ethanol, and subsequently dissolved in sterile and RNase-free microinjection TE buffer (miTE; 0.1 mM EDTA, 10 mM Tris pH 7.5). The DNA was filtered through a sterile 0.2 μm filter (Millipore, Cat. No. SLGV004SL) and the concentration was determined using the Nanodrop spectrophotometer (Thermo Scientific).

Preparation of Minicircle DNA.

4 μg of pBT346 plasmid DNA purified by the modified Qiagen mini-prep procedure above was the starting point. The 200 μl-recombination reaction consisted of 40 μl of LR clonase II (Invitrogen, Cat. No. 11791-020) and 160 μl of the DNA diluted in miTE buffer. The reaction was incubated for 3 h at 25° C. in the PCR machine. The reaction was purified using the QIAquick PCR Purification kit (Qiagen) and the DNA was eluted in 35 μl of 3-fold diluted EB (Qiagen). The DNA was digested in a 50 μl reaction with 20 U each of SacI and KpnI. The DNA was analyzed on 1% agarose gel (FIG. 5) and the minicircle DNA was purified using the MinElute Gel Extraction kit (Qiagen). The DNA was eluted in 12 μl of 3-fold diluted EB (Qiagen), filtered through a sterile 0.2 μm filter (Millipore, Cat. No. SLGV004SL) and the concentration was determined using the Nanodrop spectrophotometer (Thermo Scientific). The overall yield of the DNA with this procedure is about 3% of the starting DNA. The DNA was diluted to 6 ng/μl in miTE buffer and stored at −80° C. before injection. This DNA is more difficult to microinject than plasmid DNA.

Preparation of Mouse Genomic DNA No. 1—for Genotyping by Long-Range PCR.

Tissue samples from mouse pups (~5 mm of each tail tip) were collected in 1.5-ml tubes. Each tail was digested in 0.5 ml of lysis buffer (TrisHCl pH 8-8.5, 100 mM; EDTA pH 8, 5 mM; SDS, 0.2%; NaCl, 200 mM; proteinase K, 0.2 mg/ml) at 55° C. overnight. The digestion was centrifuged on the next day for 5 min. at ≥10,000 g, and 450 μl of the supernatant were transferred to a new tube. After adding 450 μl of 5M NaCl, the tubes were rocked for 5 min. at room temperature. The samples were centrifuged at ≥10,000 g for 10 min. 750 μl of the supernatant were transferred to a new tube and precipitated with 750 μl of isopropanol. The samples were centrifuged for 15 min at !10,000 g at room temperature. The pellet was washed with 500 μl of 70% ethanol and the tubes were air dried for 5-10 min. The pellet was dissolved in 200 μl of TE (1 mM EDTA, 10 mM Tris pH 7.5), and extracted twice with a phenol:chloroform (50:50) mix and twice with chloroform only. The DNA was precipitated with 1/10 volume of 3M sodiumacetate pH 5.2 and 2.7 volumes of ethanol, and dissolved in 200 μl of TE. 1 μl of this solution was used as template in long-range PCR (see below).

Preparation of Mouse Genomic DNA No. 2—for Genotyping by Short-Range PCR.

Tissue samples from embryos or pups (~2 mm of each tail tip) were collected in 96-well plates, so that many subsequent steps could be done with a multi-channel pipet. The plate was sealed with the plastic cover (ThermalSeal, E&K Scientific, Cat. No. 100-THER-PLT) and briefly centrifuged before the next step to make sure that the tissue samples were on the bottom of the wells. Each tissue sample was lysed with 120 μl of 50 mM NaOH. The plate was sealed with a new plastic cover, incubated in PCR machine at 95° C. for 38 min., briefly centrifuged to collect possible condensation, and the cover was peeled away. At this moment, some gas may be released from the samples and cause droplets of lysate to come close to the rim of the wells. Any solution that was close to the rim of the wells was collected by blotting it away carefully with a kimwipe. The lysates were neutralized with 30 μl of 1 M Tris (pH 7.5), tightly sealed with a new plastic seal, vortexed (using a flat head vortex), and briefly centrifuged. 1 μl of this prep was used for PCR.

Long-Range Genomic PCR:

LA Taq (Takara Bio; Cat Nos. RR02AG and RR002M) was used as well as the following primers for H11 5' arm: PR374 and PR432; H11 3' arm: PR351 and PR422; Rosa26 5' arm: Rosa3 and PR432, and Rosa26 3' arm: PR351 and PR395. The complete PCR reactions had a volume of 20 μA and contained 1 μl of genomic DNA that was prepared by the DNA preparation protocol No. 1 above. For H11 5' arm, the LA PCR buffer II was used with the following program: 94° C., 3 min., 40 cycles of: [94° C., 20 sec.; 60° C., 30 sec.; 68° C., 5 min. 30 sec.], 72° C., 15 min. For H11 3' arm, the GC buffer I was used with the following program: 94° C., 3 min., 40 cycles of: [94° C., 30 sec.; 56° C., 30 sec.; 72° C., 3 min. 30 sec.], 72° C., 15 min. For Rosa26 3' arm, the LA PCR buffer II was used with the following program: 94° C., 3 min., 40 cycles of: [94° C., 20 sec.; 58° C., 30 sec.; 68° C., 5 min.], 72° C., 15 min. For Rosa26 5' arm, the GC buffer I was used with the following program: 94° C., 3 min., 40 cycles of: [94° C., 30 sec.; 60° C., 30 sec.; 72° C., 2 min.], 72° C., 5 min.

Short-Range Genomic PCR:

All short-range PCRs were performed in 20 µl reactions containing 1 µl of prepared DNA (see Preparation of mouse genomic DNA No. 2 above), using Taq polymerase (Qiagen), and the following program: 94° C., 3 min.; 32 cycles of [94° C., 20 sec., 60° C., 25 sec., 72° C., 45 sec.]; 72° C., 5 min. Taq polymerase from Qiagen has proven more reliable than polymerases from other manufacturers with this particular DNA preparation. The products were analyzed on a 2% agarose gel.

Primer combinations and expected product sizes for the PCRs used in this study are:

PCR1 in FIG. 7 and FIG. 10; 5'-junction: PR425 and PR436. Expected sizes are: 147 bp, 217 bp, 287 bp, and 244 bp, for insertion into the first attP, second attP, third attP, or full-length attP, respectively.

PCR2 in FIG. 7 and FIG. 10; 3'-junction: PR522 and PR387. Expected sizes are: 371 bp, 301 bp, 231 bp, and 313 bp, for insertion into the first attP, second attP, third attP, or full-length attP, respectively.

PCR3 in FIG. 7; 5'-junction: PR425 and PR551. Expected sizes are 395 bp, 465 bp, 535 bp, and 492 bp, for insertion into the first attP, second attP, third attP, or full-length attP, respectively.

PCR4 in FIG. 7; 3'-junction: PR488 and PR387. In the case of cassette exchange with pBT374, expected sizes are 502 bp, 432 bp, and 362 bp, for insertion into the first attP, second attP, and third attP, respectively. For insertions of the minicircle derived from pBT346, expected sizes are: 463 bp, 393 bp, 323 bp, and 405 bp for insertion into the first attP, second attP, third attP, and full-length attP, respectively.

PCR4' in FIG. 10; 3'-junction: This PCR can be used instead of PCR4. It detects the same junction, but instead of PR488, it uses PR487. The expected sizes for minicircle insertions are: 544 bp, 474 bp, 404 bp, and 405 bp for insertion into the first attP, second attP, third attP, and full-length attP, respectively.

PCR5 in FIG. 10; 3'-junction: PR21 and PR387. Expected sizes are 498 bp, 428 bp, 358 bp, and 440 bp, for insertion into the first attP; second attP, third attP, or full-length attP, respectively. The products will be obtained only if the full plasmid is integrated.

PCR6 in FIG. 10; internal: FACS G5' and GFP2-Hermie. Expected size: 420 bp. This PCR amplifies a portion of the GFP cDNA.

PCR7+8 in FIG. 10: SH176, SH178 and PR432. The expected sizes are: 147 bp for any knockin or site-specifically integrated allele into H11 that has the unique sequence "U" at 5' end (see plasmids above), 321 bp for wt, 726 bp for H11P, and 687 bp for H11P3.

PCR9 in FIG. 10; 3' junction: PR522 and PR428. Expected sizes are: 178 bp, 248 bp, 318 bp, and 260 bp for insertion into the first attP; second attP, third attP, or full-length attP, respectively.

To confirm that a particular insertion into H11P(3) detected by PCR1 and PCR2 originated from the plasmid, an additional PCR was performed for the 3' junction, PCR5 (FIG. 10). The products were indeed obtained only when the full plasmid was integrated. This PCR was also used to test the cassette exchange founders that were positive for PCR1 and PCR2 and negative for PCR3 and PCR4. Indeed, all those founders were positive for PCR5, thereby confirming that they contain only integration of the plasmid bacterial backbone. For detection of integration into the H11PNVφ or H11P3NVφ alleles PCR1 and PCR6 were used, and instead of PCR2, PCR9 was used. For detection of any knock-in or site-specifically integrated allele into H11 PCR7+8 was used. For detection of the H11P or H11P3 Flp-out alleles, PCR8 was used.

For the majority of integrants that were analyzed in detail by sequencing of the recombinant junctions (22 out of 28 founders in Table 3), φC31 catalyzed precise recombination between attP and attB. In 6 cases, integration appeared to occur at two different attP sites, or it caused the deletion of one or more attP sites (for example, see FIG. 10, panel B, top). These imprecise events occurred only when transgenesis was performed on embryos with three tandem attP sites.

For detection of site-specific integration into R26P3NVφ PCR1 was used. For detection of any knock-in or site-specifically integrated allele into Rosa26 the following primers were used: Rosa10, Rosa11, and PR432. Expected sizes are: 168 bp for any knockin or site-specifically integrated allele into Rosa26 that has the unique sequence "U" at 5' end (see plasmids above), 330 bp for wt, and 696 bp for R26P3. For detection of the R26P or R26P3 Flp-out alleles primers Rosa10 and Rosa11 were used.

Quantitative PCR:

Quantitative PCR was performed as previously described. Each sample was tested in triplicate both for GFP and for the internal control. The primers used for GFP were: LL84 and LL85, and they generate a product of 187 bp. The internal control primers were: IMR0015 and IMR0016, and they generate a product of 200 bp.

Generation of GFP-Flpo Transgenic Mice:

GFP-Flpo mice were generated as random integrants from an experiment in which pBT340 was co-injected with φC31o mRNA into H11P3NVφ homozygous embryos of mixed background in an attempt to achieve site-specific integration of this plasmid and subsequent removal of the bacterial backbone by Flpo-mediated self-excision. The site-specific integration was not successful (0/106 F0 founders screened). However, several random insertions were retained for further characterization, in order to select an efficient Flpo line that can be detected by ubiquitous GFP expression (the progeny can be screened for GFP fluorescence with a UV lamp). The activity of one of the GFP-Flpo lines was initially evaluated by analyzing the Flp-out frequency for the H11P3NVφ allele (removal of the NVφ cassette) to create the H11P3 allele. As all F1 progeny from this founder, which was generated by a random insertion of pBT340 into H11P3NVφ homozygous embryos, were heterozygous for the H11 knock-in, the efficiency of Flp-out was established after a single cross to wt mice. All F1 progeny that were negative for GFP-Flpo, and by the nature of the cross, heterozygous for the H11 knock-in allele, were analyzed to detect H11P3 and H11P3NVφ alleles. Based on this experiment, the efficiency of Flp-out was 100%, as only H11P3 and no H11P3NVφ alleles could be detected among the F1 progeny.

Removal of Bacterial Backbone from Site-Specific Transgenes by Crossing to GFP-Flpo Mice:

The bacterial backbone can be removed from site-specific transgenes if the plasmid that was used to generate the transgene contains an FRT5 site between the 3' end of the transgene and the plasmid bacterial backbone (e.g., pBT344 or pBT366). This procedure requires two crosses: first one to create double heterozygous animals containing a site-specifically integrated allele and GFP-Flpo, and the second one to remove the GFP-Flpo transgene. For both H11P3-pCA-GFPBB and H11P3-pHb9-GFP-BB, all progeny from the second cross that did not contain GFPFlpo, but contained the site-specific integration allele, had the bacterial backbone removed (i.e., detected by genotyping as H11P3-pCA-GFP/wt and H11P3-pHb9-GFP/wt, respectively). Therefore, with this crossing scheme and our GFP-Flpo mice, the corresponding alleles without the bacterial backbone were generated at 100% efficiency.

F1 progeny from the cross of H11P3-pHb9-GFP-BB/wt (male) to GFP-Flpo (female) were also examined for possible bacterial backbone excision by maternal contribution of the Flp recombinase. Flp-out was detected in F1 animals from this cross that were positive only for the site-specifically inserted Hb9 allele.

The efficiency of the GFP-Flpo line was compared with Rosa-Flpe (Jackson Labs, Stock No. 003946). Rosa-Flpe generated Flp-out only in a small minority of F2 progeny following the two-cross scheme described above.

TABLE 1

List of primers used.

| Name of primer | SEQ ID NO |
| --- | --- |
| PR21 | SEQ ID NO: 29 |
| PR351 | SEQ ID NO: 14 |
| PR374 | SEQ ID NO: 12 |
| PR387 | SEQ ID NO: 25 |
| PR395 | SEQ ID NO: 17 |
| PR402 | SEQ ID NO: 4 |
| PR403 | SEQ ID NO: 5 |
| PR422 | SEQ ID NO: 15 |
| PR425 | SEQ ID NO: 22 |
| PR428 | SEQ ID NO: 26 |
| PR432 | SEQ ID NO: 13 |
| PR436 | SEQ ID NO: 23 |
| PR437 | SEQ ID NO: 6 |
| PR438 | SEQ ID NO: 7 |
| PR487 | SEQ ID NO: 31 |
| PR488 | SEQ ID NO: 36 |
| PR493 | SEQ ID NO: 8 |
| PR494 | SEQ ID NO: 9 |
| PR495 | SEQ ID NO: 10 |
| PR496 | SEQ ID NO: 11 |
| PR522 | SEQ ID NO: 24 |
| PR551 | SEQ ID NO: 37 |
| FACS G5' | SEQ ID NO: 27 |
| GFP2-Hermie | SEQ ID NO: 28 |
| IMR0015 | SEQ ID NO: 34 |
| IMR0016 | SEQ ID NO: 35 |
| LL84 | SEQ ID NO: 32 |
| LL85 | SEQ ID NO: 33 |
| Rosa10 | SEQ ID NO: 20 |
| Rosa11 | SEQ ID NO: 21 |
| Rosa3 | SEQ ID NO: 16 |
| SH176 | SEQ ID NO: 18 |
| SH178 | SEQ ID NO: 19 |

Example 1

Pronuclear Injection in Mice

FIG. 1, panel A depicts a method for site-specific transgenesis in mice via pronuclear microinjection of a DNA/RNA mix into mouse zygotes. Both H11 and R26 loci were modified with attP sites (note the different orientation of attP sites for the two loci), but for simplicity, the scheme in FIG. 1, panel A illustrates the process for H11 only.

The method utilized the ϕC31 integrase from a Streptomyces phage and its recognition sites (attB and attP) to catalyze recombination between an attB site from a circular recombinant DNA, and an attP site that was inserted at a specific locus in the mouse genome. As discussed below, the method efficiently produced transgenic mice containing a site-specifically integrated single-copy transgene that was expressed globally from a ubiquitous promoter.

To generate embryos containing attP sites for ϕC31 integrase-mediated transgenesis, standard homologous recombination-based methods were used in mouse ES cells (T. Doetschman et al. (1987) Nature 330:576; M. R. Capecchi (1989) Science 244:1288). Three shortened tandem ϕC31 integrase attP sites (attPx3) or a single "full length" attP site (Groth et al. (2000) Proc Natl Acad Sci USA 97:5995) was inserted into two loci: the Rosa26 (R26) locus on mouse chromosome 6 (P. Soriano (1999) Nat Genet. 21:70) and an intergenic Hipp11 (H11) locus on mouse chromosome 11 (FIG. 1, panel A).

The R26 locus supports global marker expression of a single copy knockin transgene driven by a combination of the CMV enhancer and the chicken β-actin promoter (pCA). Knockin experiments confirmed that H11 supports high-level global marker expression from the pCA promoter.

The knockin cassettes used herein also contained a mammalian codon-optimized ϕC31 integrase (ϕC31o) (C. S. Raymond and P. Soriano (2007) PLoS ONE 2, e162) driven by a fragment of the mouse VASA promoter sufficient for germline expression, and a neomycin-resistance gene, flanked by FRT5 sites (FIG. 3). This "VASA cassette" was designed to provide the integrase in embryos in situ. Referring to FIG. 3, (1) is a schematic of the recombinant DNA construct for introduction of attP sites and NVϕ cassette into H11 via homologous recombination in mouse ES cells. Two versions containing either a single "full-length" attP site or three tandem shorter attP sites were generated. (2) depicts mouse chromosome 11 with H11 designated as a triangle; (3) depicts the H11P3NVϕ locus resulting from homologous recombination; (4) illustrates the H11P3 locus that was generated from (3), by Flpo mRNA injection into the cytoplasm of mouse embryos carrying (3).

The modified ES cells were used to produce chimeric mice, and mice with germline-transmitted alleles were used to establish mouse colonies homozygous for the knockin cassettes.

Example 2

Cassette Exchange DNA Insertion in Mice

As an alternative to insertion of DNA at a single attP site, a plasmid in which pCA-GFP is flanked by two attB sites (pattB-pCA-GFP-attB) was injected into H11P3 homozygous embryos. This approach allows ϕC31 integrase to catalyze a recombinase-mediated cassette exchange reaction (FIG. 7, bottom right). Integration of the circular pattB-pCA-GFP-attB plasmid into H11P3 was tested, and resulted in successful cassette exchange as confirmed by PCR (FIG. 7, bottom right, and Table 2, row 4). In these experiments, insertion of a full plasmid was never detected. The integrated transgenes were properly transmitted from founders to progeny (Table 3). Both the cassette-exchange strategy and the strategy described above in Example 1 resulted in broad and high-level GFP expression in pCA-GFP transgenic mice (FIG. 7, right, FIG. 8, panel D, and FIG. 10, panel C, bottom).

TABLE 2

Efficiency of site-specific integration.

| Row | DNA* | DNA type | DNA size, kb | Strain | Background | F0 (n) | SS F0 (n) | Signl·cance¶ | SS, % (of F0) | R F0 (n) | R, % (of F0) |
|---|---|---|---|---|---|---|---|---|---|---|---|
| 1 | attB-pCA-GFP | Minicircle | ·3 | H11P | Mix | 21 | 1 | NS vs. row 2 | 4.8 | 1 | 4.8 |
| 2 | attB-pCA-GFP | Minicircle | ·3 | H11P3 | Mix | 39 | 4 | | 10.3 | 1 | 2.6 |
| 3 | attB-pCA-GFP | Minicircle | ·3 | H11P3 | FVB N4 | 15 | 6 | P · 0.05 vs. row 2 | 40.0 | 3 | 20.0 |
| 4 | attB-pCA-GFP-attB | Plasmid | ·6 | H11P3 | FVB N4 | 38‡ | 6$^k$ | — | 15.8 | 1 | 2.6 |
| 5 | attB-pCA-GFP, no RNA | Plasmid | ·6 | H11P3NV· | Mix | 32‡ | 0 | — | 0.0 | 5 | 15.6 |
| 6 | attB-pCA-GFP | Plasmid | ·6 | H11P3NV· | Mix | 64§ | 10 | NS vs. row 7 | 15.6 | 4 | 6.3 |
| 7 | attB-pCA-GFP | Plasmid | ·6 | H11PNV· | Mix | 30‡ | 2 | | 6.7 | 0 | 0.0 |
| 8 | attB-pCA-GFP-FRT5 | Plasmid | ·6 | H11P | Mix | 51 | 5 | NS vs. row 9 | 9.8 | 3 | 5.9 |
| 9 | attB-pCA-GFP-(FRT5)† | Plasmid | ·6 | H11P3 | Mix | 61 | 4 | | 6.6 | 9 | 14.8 |
| 10 | attB-pCA-GFP-FRT5 | Plasmid | ·6 | H11P3 | FVB N4 | 8 | 3 | P · 0.05 vs. row 9 | 37.5 | 1 | 10.3 |
| 11 | attB-pHB9-GFP-FRT5 | Plasmid | ·14 | H11P3 | FVB N4 | 66 | 2 | — | 3.0 | 2 | 3.0 |
| 12 | attB-pCA-GFP | Plasmid | ·6 | R26P3NV· | Mix | 22‡ | 2 | — | 9.1 | 2 | 9.1 |

Abbreviations:

F0, embryos or animals obtained from injections;

SS, site-specific integration;

R, random integration;

mix, mixed background of 129, C57BL/6 and DBA2;

FVB N4, mice of the mixed background were outcrossed for 4 generations to the FVB strain and then intercrossed.

*All DNA was coinjected with φC31o mRNA, except for row 5.

†Both FRT and non-FRT versions of attB-pCA-GFP were used.

‡F0s were analyzed only as E10 or E11 embryos.

§F0s were analyzed either as E10 or E11 embryos or as live pups.

$^k$The six founders listed contained pCA-GFP without the bacterial backbone; five more founders with cassette exchange contained only the bacterial backbone. Therefore, the total number of founders with cassette exchange is 11 (29%).

¶Fisher's exact test.

NS, not significant.

TABLE 3

Complete list of transgenic founders (n = 28) and their germline transmission efficiency.

| Transgene | Founder | Background | Sex | Insertion into attP 1, 2 or 3 | GT of SS (Y/N)$^a$ | N1 (n) | N1 SS (n) | N1 SS (%)$^c$ | N2/3 (n) | N2/3 SS (n) | N2/3 SS (%) | R (Y) | N1 R (n) | N1 R (%) |
|---|---|---|---|---|---|---|---|---|---|---|---|---|---|---|
| H11P3-pCA-GFP-BB-NVφ | A1 | mix | M | 1/3$^b$ | Y | 55 | 36 | 65.5 | 25 | 15 | 60.0 | | 0 | 0 |
| | A2 | mix | M | 3 | Y | 62 | 12 | 19.4*** | 16 | 10 | 62.5 | | 0 | 0 |
| | A3 | mix | M | 1/3$^b$ | Y | 36 | 10 | 27.8* | | | | | 0 | 0 |
| | A4 | mix | M | 3 | Y | 63 | 29 | 46.0 | 14 | 4 | 28.6 | | 0 | 0 |
| H11P3-pCA-GFP-BB | B1 | mix | M | 3 | Y | 143 | 19 | 13.3*** | 48 | 20 | 41.7 | Y | 11 | 7.7 |
| | B2 | mix | M | 2/3$^b$ | Y | 29 | 11 | 37.9 | 85 | 36 | 42.4 | | 0 | 0 |
| | B3 | mix | Fem | 2 | Y | 44 | 9 | 20.5*** | 76 | 34 | 44.7 | | 0 | 0 |
| | B4 | mix | Fem | 2 | Y | 20 | 4 | 20.0* | | | | | 0 | 0 |
| | B5 | FVB N4 | M | 2 | Y | 24 | 9 | 37.5 | | | | | 0 | 0 |
| | B6 | FVB N4 | Fem | 2 | N | | | | | | | | 0 | 0 |
| | B7 | FVB N4 | Fem | 2/3$^b$ | Y | 8 | 3 | 37.5 | | | | Y | 3 | 37.5 |
| H11P-pCA-GFP-BB | C1 | mix | Fem | n/a | Y | 15 | 11 | 73.3 | | | | | 0 | 0 |
| | C2 | mix | M | n/a | Y | 44 | 9 | 20.5*** | | | | | 0 | 0 |
| | C3 | mix | Fem | n/a | Y | 9 | 4 | 44.4 | | | | Y | 2 | 22.2 |
| | C4 | mix | Fem | n/a | N | 1 | 0 | 0 | | | | | 0 | 0 |
| | C5 | mix | M | n/a | Y | 67 | 14 | 20.9*** | 62 | 29 | 46.8 | | 0 | 0 |
| H11P3-pCA-GFP | D1 | mix | Fem | 1/2$^b$ | Y | 20 | 8 | 40.0 | 25 | 15 | 60.0 | | 0 | 0 |
| | D2 | mix | M | 3 | Y | 33 | 10 | 30.3 | 12 | 4 | 33.3 | | 0 | 0 |
| | D3 | mix | Fem | 3 | Y | 23 | 5 | 21.7* | | | | | 0 | 0 |
| | D4 | mix | M | 3 | N | 59 | 0 | 0*** | | | | | 0 | 0 |
| | D5 | FVB N4 | Fem | 3 | Y | 32 | 6 | 18.8** | | | | | 0 | 0 |
| | D6 | FVB N4 | Fem | 3 | Y | 41 | 10 | 24.4** | | | | | 0 | 0 |
| | D7 | FVB N4 | M | 3 | N | | | | | | | | 0 | 0 |
| | D8 | FVB N4 | Fem | 3 | Y | 14 | 2 | 14.3* | | | | | 0 | 0 |
| | D9 | FVB N4 | M | 1/3$^b$ | N | | | | | | | | 0 | 0 |
| | D10 | FVB N4 | Fem | 2 | Y | 27 | 8 | 29.6 | 20 | 10 | 50.0 | | 0 | 0 |
| H11P-pCA-GFP | E1 | mix | M | n/a | Y | 39 | 11 | 28.2* | | | | | 0 | 0 |

TABLE 3-continued

Complete list of transgenic founders (n = 28) and their germline transmission efficiency.

| Transgene | Founder | Background | Sex | Insertion into attP 1, 2 or 3 | GT of SS (Y/N)[a] | N1 (n) | N1 SS (n) | N1 SS N1 SS (%)[c] | N2/3 (n) | N2/3 SS (n) | N2/3[d] SS (%) | R (Y) | N1 R (n) | N1 R (%) |
|---|---|---|---|---|---|---|---|---|---|---|---|---|---|---|
| H11P-pHB9-GFP | F1 | FVB N4 | Fem | 2 | Y | 45 | 9 | 20.0*** | | | | | 0 | 0 |

Abbreviations:
SS, site-specific integration;
R, random integration;
GT, germline transmission;
mix, mixed background of 129, C57BL/6 and DBA2;
FVB N4, the mice of the mixed background were outcrossed for 4 generations to the FVB strain and then intercrossed;
N1, progeny from the first generation where a founder was crossed to CD1 wt animal;
N2 or N3, progeny from the second or third generation where N1 or N2 animals were crossed to CD1 wt animals, respectively.
[a]The founders that did not transmit were ether sterile (D7 and D9), died upon delivery (C4), or cannibalized the pups (B6).
[b]Based on site-specific PCR, integration appeared to occur at two different attP sites, or it caused the deletion of one or more attP sites.
[c]Frequency of germline transmission for site-specific integrations from some founders was sub-Mendelian, suggesting mosaicism in the founders (Fisher's exact test, *p < 0.05; p < 0.01; *p < 0.001).
[d]Frequency of transmission for site-specific integrations for subsequent generations (N2 and/or N3) is statistically indistinguishable from Mendelian transmission (Fisher's exact test).

Example 3

PCR Test for Transgene Integration into the H11 Locus

A series of experiments were carried out to test integration of transgenes at the knocked-in attP sites. First, a circular plasmid, pattB-pCA-GFP, was injected into embryos homozygous for attPx3 and the VASA cassette knocked-in at the H11 locus (H11P3NVφ). The injected plasmid contained a "full-length" attB site and the sequence for a thermotolerant GFP (Siemering K R et al. (1996) *Curr Biol* 6:1653; Okada A et al. (1999) *Exp Neurol* 156:394) driven by the ubiquitous pCA promoter (FIG. 1, panel $B_1$). F0 embryos were analyzed at embryonic day 10 or 11 (E10/E11) by PCR to detect newly-formed junctions due to site-specific insertions (FIG. 1, panel $B_2$). Site-specific integrations (0/32 F0s; Table 2) were not detected despite occasional random integrations. It was possible that the VASA promoter did not promote sufficient φC31o expression to enable site-specific insertions. In vitro transcribed mRNA for φC31o was then co-injected with the pattB-pCA-GFP plasmid into homozygous H11P3NVφ embryos. These experiments yielded site-specific integrations (FIG. 1, panel $B_2$; Table 2), indicating that site-specific integrase-mediated integration of transgenes was achieved with exogenously supplied φC31o mRNA.

Because the VASA cassette did not provide sufficient integrase activity in situ, the H11P3 allele was produced, where the VASA cassette from H11P3NVφ had been excised by FLPo-mediated recombination (FIG. 3). In a second series of experiments, pattB-pCA-GFP and φC31o mRNA were co-injected into homozygous H11P3 embryos. These experiments also produced site-specific integrants (FIG. 1, panel $C_1$, left and Table 2). All site-specific founder pups derived from injecting pattB-pCA-GFP into H11P3NVφ or H11P3 expressed GFP when examined as embryos. Moreover, integrated transgenes were properly transmitted from founders to progeny (Table 2).

TABLE 4

Efficiency of site-specific integration.

| DNA[a] | DNA type | DNA size (kb) | Strain | Background | F0 (n) | SS F0 (n) | Significant?[d] | SS % (from F0) | R F0 (n) | R % (from F0) |
|---|---|---|---|---|---|---|---|---|---|---|
| pattB-pCA-GFP, no RNA | plasmid | ~6 | H11P3NVφ | mix | 32[b] | 0 | | 0.0 | 5 | 15.6 |
| pattB-pCA-GFP | plasmid | ~6 | H11PNVφ | mix | 30[b] | 2 | ⎫ ns | 6.7 | 0 | 0.0 |
| pattB-pCA-GFP | plasmid | ~6 | H11P3NVφ | mix | 64[c] | 10 | ⎭ | 15.6 | 4 | 6.3 |
| pattB-pCA-GFP | plasmid | ~6 | R26P3NVφ | mix | 22[b] | 2 | | 9.1 | 2 | 9.1 |
| pattB-pCA-GFP-FRT5 | plasmid | ~6 | H11P | mix | 51 | 5[f] | ⎫ ns | 9.8 | 3 | 5.9 |
| pattB-PCA-GFP-(FRT5)[e] | plasmid | ~6 | H11P3 | mix | 61 | 4[f] | ⎭ ⎫ * | 6.6 | 9 | 14.8 |
| pattB-pCA-GFP-FRT5 | plasmid | ~6 | H11P3 | FVB N4 | 8 | 3[f] | ⎭ | 37.5 | 1 | 10.3 |

TABLE 4-continued

Efficiency of site-specific integration.

| DNA[a] | DNA type | DNA size (kb) | Strain | Background | F0 (n) | SS F0 (n) | Significant?[d] | SS % (from F0) | R F0 (n) | R % (from F0) |
|---|---|---|---|---|---|---|---|---|---|---|
| attB-pCA-GFP (MC) | minicircle | ~3 | H11P | mix | 21 | 1 | } ns | 4.8 | 1 | 4.8 |
| attB-pCA-GFP (MC) | minicircle | ~3 | H11P3 | mix | 39 | 4 | } * | 10.3 | 1 | 2.6 |
| attB-pCA-GFP (MC) | minicircle | ~3 | H11P3 | FVB N4 | 15 | 6 | | 40.0 | 3 | 20.0 |

Abbreviations:
SS, site-specific integration;
R, random integration;
mix, mixed background of 129, C57BL/6 and DBA2;
FVB N4, mice of the mixed background were backcrossed for 4 generations to the FVB strain and then intercrossed.
[a]All DNA was coinjected with φC31o mRNA, except where indicated.
[b]F0s were analyzed only as E10 or E11 embryos.
[c]F0s were analyzed either as E10 or E11 embryos or as live pups.
[d]Statistical significance for transgenesis efficiency was evaluated using Fisher's exact test.
ns, not-siginificant;
* p < 0.05.
[e]Both FRT and non-FRT versions of pattB-pCA-GFP were used.

TABLE 5

Transmission of site-specifically integrated transgenes.

| Transgene | Founder | Background | Sex | Insertion into attP 1, 2 or 3 | Germline transmission of SS transgene (Y/N) | F1 (n) | F1 SS (n) | F1[d] SS (%) | F2/3 (n) | F2/3 SS (n) | F2/3[e] SS (%) | Random insertion (Y) | F1 R (n) | F1 R(%) |
|---|---|---|---|---|---|---|---|---|---|---|---|---|---|---|
| H11P3-pCA-GFP-BB-NVφ | A1 | mix | M | 1[c] | Y | 55 | 36 | 65.5 | 25 | 15 | 60.0 | | 0 | 0 |
| | A2 | mix | M | 3 | Y | 62 | 12 | 19.4*** | 16 | 10 | 62.5 | | 0 | 0 |
| | A3 | mix | M | 1[c] | Y | 36 | 10 | 27.8* | | | | | 0 | 0 |
| | A4 | mix | M | 3 | Y | 63 | 29 | 46.0 | 14 | 4 | 28.6 | | 0 | 0 |
| H11P3-pCA-GFP-BB | B1 | mix | M | 3 | Y | 143 | 19 | 13.3*** | 48 | 20 | 41.7 | Y | 11 | 7.7 |
| | B2 | mix | M | 2/3[c] | Y | 29 | 11 | 37.9 | 85 | 36 | 42.4 | | 0 | 0 |
| | B3 | mix | Fem | 2 | Y | 44 | 9 | 20.5*** | 76 | 34 | 44.7 | | 0 | 0 |
| | B4 | mix | Fem | 2 | Y | 20 | 4 | 20.0* | | | | | 0 | 0 |
| | B5 | FVB N4 | M | 2 | Y | 24 | 9 | 37.5 | | | | | 0 | 0 |
| | B6 | FVB N4 | Fem | 2 | N[a] | | | | | | | | | |
| | B7 | FVB N4 | Fem | 2/3[c] | Y | 8 | 3 | 37.5 | | | | Y | 3 | 37.5 |
| H11P-pCA-GFP-BB | C1 | mix | Fem | n/a | Y | 15 | 11 | 73.3 | | | | | 0 | 0 |
| | C2 | mix | M | n/a | Y | 44 | 9 | 20.5*** | | | | | 0 | 0 |
| | C3 | mix | Fem | n/a | Y[b] | 9 | 4 | 44.4 | | | | Y | 2 | 22.2 |
| | C4 | mix | Fem | n/a | N (died) | 1 | 0 | 0 | | | | | 0 | 0 |
| | C5 | mix | M | n/a | Y | 67 | 14 | 20.9*** | 62 | 29 | 46.8 | | 0 | 0 |
| H11P3-pCA-GFP | D1 | mix | Fem | 1[c] | Y | 20 | 8 | 40.0 | 25 | 15 | 60.0 | | 0 | 0 |
| | D2 | mix | M | 3 | Y | 33 | 10 | 30.3 | 12 | 4 | 33.3 | | 0 | 0 |
| | D3 | mix | Fem | 3 | Y | 23 | 5 | 21.7* | | | | | 0 | 0 |
| | D4 | mix | M | 3 | N | 59 | 0 | 0*** | | | | | 0 | 0 |
| | D5 | FVB N4 | Fem | 3 | Y | 32 | 6 | 18.8** | | | | | 0 | 0 |
| | D6 | FVB N4 | Fem | 3 | Y | 41 | 10 | 24.4** | | | | | 0 | 0 |
| | D7 | FVB N4 | M | 3 | N (sterile) | | | | | | | | | |
| | D8 | FVB N4 | Fem | 3 | Y | 14 | 2 | 14.3* | | | | | 0 | 0 |
| | D9 | FVB N4 | M | 1[c] | N (sterile) | | | | | | | | | |
| | D10 | FVB N4 | Fem | 2 | Y | 27 | 8 | 29.6 | 20 | 10 | 50.0 | | 0 | 0 |
| H11P-pCA-GFP | E1 | mix | M | n/a | Y | 39 | 11 | 28.2* | | | | | 0 | 0 |

Abbreviations:
SS, site-specific integration;
R, random integration;
mix, mixed background of 129, C57BL/6 and DBA2;
FVB N4, the mice of the mixed background were for backcrossed for 4 generations to the FVB strain and then intercrossed.
[a]Pups died twice.
[b]Died during delivery.
[c]Based on site-specific PCR, integration appeared to occur at two different attP sites, or it caused the deletion of one or more attP sites.
[d]Frequency of transmission for site-specific integrations for some founders is sub-Mendelian, suggesting mosaicism in the founders (Fisher's exact test, *p < 0.05; p < 0.01; *p < 0.001).
[e]Frequency of transmission for site-specific integrations for subsequent generations (F2 and/or F3) is statistically indistinguishable from Mendelian transmission (Fisher's exact test)

Example 4

GFP Expression of Mice Containing the Transgene at the H11 Locus

Despite proper transmission of the site-specifically integrated transgenes, GFP expression levels in the progeny of these transgenic founders exhibited a wide range in embryos (FIG. 1, panel D) and adult tails. Moreover, the GFP expression in the progeny was mosaic in several internal tissues including the heart, brain, and particularly the liver (FIG. 2, panel A; FIG. 4).

Referring to FIG. 2, panel A are representative fluorescence microscopy images from liver, heart and cerebellum of F1 or F2 animals for the genotypes shown on top. The livers and hearts are represented by epifluorescence images of 10 µm sections stained only by DAPI. The green signal is GFP fluorescence. The cerebella are represented by confocal images of sections stained by anti-GFP antibody and anti-calbindin for Purkinje cells. Panel B is the average fluorescence in the GFP channel for liver sections of the genotypes shown below. The number of individual animals and founders analyzed for each genotype are listed below the genotypes. When samples from multiple founders were combined to obtain an average, each founder was represented by the same number of animals except in the case labeled by a spade. Mouse designations are numbers used to represent each mouse in FIG. 4.

Referring to FIG. 4, the animals were grouped by genotype and founder (as designated below the graph in FIG. 4). For each founder, the one of the three sites from H11P3 into which the site-specific integration occurred is indicated below. In cases labeled by spades, recombination appeared to occur at two different attP sites, or it resulted in deletion of some of the attP sites. For a subset of animals, representative images of liver sections are shown below. For a subset of those, the corresponding images of heart and cerebellar sections are included as well. The numbers below the images correspond to the numbers of individual animal numbers from the chart. Of the three tissues examined in detail, the cerebellar Purkinje cells (counterstained in red with a Purkinje-cell specific marker calbindin) appear to be least sensitive to expression variability. The cells in animals #8 and #27 that are calbindin+ but GFP- are indicated by asterisks. Liver is the most sensitive to expression variability in the presence of the BB and/or the VASA cassette. Animals #36-54 (19 total with no VASA cassette or the BB) show uniform GFP expression except animals #36 (the strongest variability observed in this set) and #38.

This variable and mosaic expression was first observed with H11P3NVφ as the host. It was possible that the nearby germline-specific VASA promoter affected the expression of the pCA-GFP introduced into H11 through integrase-mediated transgenesis. Indeed, pCA-GFP transgenes produced in H11P3 host, where the VASA cassette had been removed, produced more uniform GFP expression (FIG. 1, panel D, compare the first row with second row; FIG. 2, panel A, compare the $2^{nd}$ column with the $1^{st}$ column; FIG. 4). However, considerable variability in pCA-GFP transgene expression still persisted especially in the livers (FIG. 2, panel A) of F1 or F2 animals derived from a number of transgenic founders (FIG. 4).

Plasmid bacterial backbone (BB) in extrachromosomal (episomal) transgenes could silence the rest of the covalently linked DNA by recruitment of heterochromatic factors. To test if the bacterial DNA backbone that was part of the integrated transgene contributed to the variability of GFP expression, an in vitro system for producing minicircle DNA—circular DNA containing desired transgene elements but devoid of the BB was developed (FIG. 5). From left to right in FIG. 5, panel A: The starting plasmid (pBT346) contains λ attL and attR sites, which recombine in the LR clonase-catalyzed reaction to generate two minicircles: one (MC) contains the φC31 attB site and pCA-GFP, and the other contains the plasmid bacterial backbone (BB). After recombination, the DNA is treated with appropriate restriction endonucleases to selectively digest the BB minicircle and the starting plasmid. The recombined and digested DNA is run on 1% agarose gel (FIG. 5, panel B). MC DNA (arrow on the gel) migrates faster than the linear BB or plasmid DNA and is purified from the gel for microinjection The minicircle DNA was injected into H11P3 embryos to produce transgenic animals (FIG. 1, panel $C_1$, right). For simplicity, hereafter, mice derived from integration of the entire pCA-GFP plasmid (which contains the BB) were designated as pCA-GFP-BB (FIG. 1, panel $C_1$ left), and mice derived from integration of the pCA-GFP minicircle were designated as pCA-GFP (FIG. 1, panel $C_1$, right). Transgenic animals derived from the pCA-GFP minicircle exhibited higher and much more uniform expression in all tissues examined, including the liver (FIG. 1, panel D, bottom row; FIG. 2, panel A, $3^{rd}$ column; FIG. 4).

Example 5

Removal of Bacterial Backbone from Site-Specific Transgenes by Crossing to GFP-FLPo Mice The removal of bacterial backbone from the pCA-GFP-BB transgene by crossing to GFP-FLPo transgenic mice also resulted in elevated transgene expression (FIG. 11).

The bacterial backbone can be removed from site-specific transgenes if the plasmid that was used to generate the transgene contains an FRT5 site between the 3' end of the transgene and the plasmid bacterial backbone (e.g., pBT344 or pBT366). This procedure required two crosses: the first cross created double heterozygous animals containing a site-specifically integrated allele and GFP-Flpo, and the second cross removed the GFP-Flpo transgene. For both H11P3-pCA-GFP-BB and H11P3-pHb9-GFP-BB, all progeny from the second cross that did not contain GFP-Flpo, but contained the site-specific integration allele, had the bacterial backbone removed (i.e., detected by genotyping as H11P3-pCA-GFP/wt and H11P3-pHb9-GFP/wt, respectively). Therefore, using this crossing scheme and the GFP-Flpo mice, the corresponding alleles without the bacterial backbone were generated at 100% efficiency.

F1 progeny from the cross of H11P3-pHb9-GFP-BB/wt (male) to GFP-Flpo (female) were also examined for possible bacterial backbone excision by maternal contribution of the Flp recombinase. No Flp-out was detected in F1 animals from this cross that were positive only for the site-specifically inserted Hb9 allele.

Example 6

Sources of GFP Expression Variability in Mice Containing the Transgene at the H11 Locus These data above demonstrated that pCA-GFP at the H11 locus expressed GFP ubiquitously in the absence of the VASA cassette and the BB. Since the greatest variability was observed in the liver, liver was used as a model to determine the relative contributions of the VASA cassette and the BB to GFP expression variability in these transgenic mice (FIG. 2, panel A; FIG. 4). In addition, to test for the possible differences between single attP vs. attPx3, and to probe the effect of genetic background, transgenic mice starting from H11P, or H11P3 mice that had been outcrossed to the FVB strain for 4 generations were generated. Total GFP fluorescence of liver sections from different transgenic animals was compared under identical conditions. The number of individual animals and founders analyzed for each genotype are listed below the genotypes in FIG. 6. When samples from multiple founders were combined to obtain an average, each founder was represented by the same number of animals except in the case labeled by a spade. Mouse designations are numbers used to represent each mouse in FIG. 4. Statistical comparisons were performed with two-tailed unequal variance Student's t-test (Welch's t-test; ns, p>0.2). The GFP fluorescence was found to be not affected by the genetic background of the donor embryos.

There were no statistically significant differences in GFP fluorescence between transgenes that differed only in the number of attP copies or in the genetic background of the strain for transgenesis (compare $1^{st}$ vs. $2^{nd}$ column, and $4^{th}$ vs. $5^{th}$ column in FIG. 6). Therefore, all data were segregated only according to the presence of the VASA cassette and/or the BB (FIG. 2, panel B).

In the presence of both the VASA cassette and the BB, GFP expression was detectable in the liver in a small number of cells and at a very low level (FIG. 2, panel A, top left), but was statistically indistinguishable from negative controls when total fluorescence is compared quantitatively (FIG. 2, panel B, compare $2^{nd}$ and $1^{st}$ columns). However in other organs analyzed (heart and brain), GFP expression was apparent but mosaic (FIG. 2, panel A; FIG. 4). When the VASA cassette was removed but the BB was still present, GFP fluorescence intensity became significantly higher (FIG. 2, panel B, compare $3^{rd}$ and $2^{nd}$ columns). Finally, when the BB was removed, GFP fluorescence intensity was even higher than that from transgenes containing only the BB (FIG. 2, panel B, compare $4^{th}$ and $3^{rd}$ columns). Thus, both the VASA cassette and the BB significantly affected transgene expression. The reduction of total fluorescence intensity could be caused by low level of expression in every cell, absence of expression in a subset of cells, or a combination of the above. As is evident from FIG. 2, panel B and FIG. 4, both factors contribute to the reduced level of transgene expression in the presence of the VASA cassette or the BB. In summary, the minicircle approach was essential for removing the remaining expression variability.

Example 7

Tissue-Specific Expression of Transgenes in H11

To test if a tissue-specific promoter could provide appropriate expression using the disclosed transgenesis method, pattB-pHb9-GFP-FRT5 was integrated into H11P3 (Table 1, row 11). This plasmid contains an approximately 9-kb promoter fragment from the murine transcription factor Hb9 gene that has been shown to be sufficient to direct appropriate tissue- and cell-specific expression in transgenic animals. Tissue-specific marker expression was examined before and after removal of the bacterial backbone by using the GFP-FLPo transgene (See Materials and Methods, FIG. 9, panel A). In agreement with previously reported expression patterns, GFP expression was observed in motor neurons in the ventral spinal cord and the tail tip (FIG. 9, panel B). In this case, the removal of bacterial backbone did not appear to affect the expression level of the transgene (FIG. 9, panel C). Double-labeling with endogenous Hb9 protein confirmed the motor neuron-specific expression of the transgene (FIG. 9, panel C).

Example 8

Integration Efficiency

Comparisons of the integration efficiency for attP-modified loci were made, expressed as the percentage of F0 animals with site-specific integrations obtained from the total number of F0s (Table 2; Table 6 provides more details). Although in pooled data (Table 7), H11P3 (three copies of shortened attP) appeared somewhat more efficient than H11P (one copy of the full-length attP), the efficiencies of site-specific insertions into these two loci were statistically indistinguishable (Table 7, compare rows 1 vs. 2; and Table 2, compare rows 1 vs. 2, 6 vs. 7, and 8 vs. 9). In contrast, outcrossing the H11P3 mice to the FVB strain for four generations (FVB N4) significantly increased the integration efficiency to approximately 40% (Table 2, compare rows 2 vs. 3 and 9 vs. 10; Table 7, compare rows 2 vs. 3). This efficiency is comparable to or better than the efficiency of traditional transgenesis with random integration. Circular DNAs with sizes from 3 to 6 kb appeared to have similar efficiencies of integration (Table 2), but larger DNA (14 kb) showed decreased integration efficiency (~3%; Table 2, row 11). The efficiency of cassette exchange by using H11P3 is approximately 30%, but because identical attB sites in the plasmid and identical attP sites in the genome were used, cassette exchange could result in either integration of the transgene of interest or the bacterial backbone. Therefore, only half of the cassette-exchange insertions (~16%) contained GFP and the other half contained the plasmid backbone (Table 2, row 4).

Although circular DNA was used for injections, insertions were also observed at locations other than the intended attP sites (Table 2). In 20 of 23 founders that transmitted their site-specific transgenes to the progeny, the site-specific integrants contained a single-copy transgene and did not contain a second random insertion as judged by PCR and quantitative PCR (Materials and Methods). In rare cases, when site-specific and random integration occurred in the same transgenic founder, the two distinct transgene integrations could be readily segregated in the N1 progeny.

TABLE 6

Stepwise efficiency of site-specific integration.

| Row | DNA[a] | DNA type | DNA size (kb) | Strain | Background | Embryos injected (n) | Embryos implanted (n) | Implanted/injected (%) |
|---|---|---|---|---|---|---|---|---|
| 1 | attB-pCA-GFP | minicircle | ~3 | H11P | mix | 141 | 115 | 82 |
| 2 | attB-pCA-GFP | minicircle | ~3 | H11P3 | mix | 168 | 136 | 81 |
| 3 | attB-pCA-GFP | minicircle | ~3 | H11P3 | FVB N4 | 122 | 115 | 94 |

TABLE 6-continued

Stepwise efficiency of site-specific integration.

| Row | | | | | | | | |
|---|---|---|---|---|---|---|---|---|
| 4 | attB-pCA-GFP-attB | plasmid | ~6 | H11P3 | FVB N4 | 128 | 119 | 93 |
| 5 | attB-pCA-GFP, no RNA | plasmid | ~6 | H11P3NVφ | mix | 160 | 78 | 49 |
| 6 | attB-pCA-GFP | plasmid | ~6 | H11P3NVφ | mix | 292 | 223 | 76 |
| 7 | attB-pCA-GFP | plasmid | ~6 | H11PNVφ | mix | 140 | 89 | 64 |
| 8 | attB-pCA-GFP-FRT5 | plasmid | ~6 | H11P | mix | 264 | 232 | 88 |
| 9 | attB-pCA-GFP-(FRT5)[b] | plasmid | ~6 | H11P3 | mix | 142 | 129 | 91 |
| 10 | attB-pCA-GFP-FRT5 | plasmid | ~6 | H11P3 | FVB N4 | 50 | 43 | 86 |
| 11 | attB-pCA-GFP-FRT5 | plasmid | ~14 | H11P3 | FVB N4 | 305 | 267 | 88 |
| 12 | attB-pCA-GFP | plasmid | ~6 | R26P3NVφ | mix | 83 | 63 | 76 |

| Row | F0 (n) | F0/ implanted (%) | SS (n) | SS % (of injected) | SS % (of implanted) | SS % (of F0) | R (n)[h] | R % (of implanted) | R % (of F0) | Experiments (n) |
|---|---|---|---|---|---|---|---|---|---|---|
| 1 | 21 | 18 | 1 | 0.7 | 0.9 | 4.8 | 1 | 0.9 | 4.8 | 4 |
| 2 | 39 | 29 | 4 | 2.4 | 2.9 | 10.3 | 1 | 0.7 | 2.6 | 4 |
| 3 | 15 | 13 | 6 | 4.9 | 6.2 | 40.0 | 3 | 2.6 | 20.0 | 3 |
| 4 | 38[e] | 32 | 6[e] | 15.8 | 5.0 | 15.8 | 1 | 0.9 | 2.6 | 1 |
| 5 | 32[e] | 41 | 0 | 0.0 | 0.0 | 0.0 | 5 | 6.4 | 15.6 | 1 |
| 6 | 64[d] | 29 | 10 | 3.4 | 4.5 | 15.6 | 4 | 1.8 | 6.3 | 3 |
| 7 | 30[e] | 34 | 2 | 1.4 | 2.2 | 6.7 | 0 | 0.0 | 0.0 | 2 |
| 8 | 51 | 22 | 5[f] | 1.9 | 2.2 | 9.8 | 3[g] | 0.9 | 5.9 | 5 |
| 9 | 61 | 47 | 4[f] | 2.8 | 3.1 | 6.6 | 9[g] | 9.9 | 14.8 | 4 |
| 10 | 8 | 19 | 3[f] | 6.0 | 7.0 | 37.5 | 1[g] | 0.0 | 10.3 | 1 |
| 11 | 66[d] | 25 | 2[f] | 0.7 | 0.7 | 3.0 | 2[g] | 0.7 | 3.0 | 2 |
| 12 | 22[e] | 35 | 2 | 2.4 | 3.2 | 9.1 | 2 | 3.2 | 9.1 | 1 |

Abbreviations:
F0, embryos or animals obtained from injections;
SS, site-specific integration;
R, random integration;
mix, mixed background of 129, C57BL/6 and DBA2;
FVB N4, mice of the mixed background were outcrossed for 4 generations to the FVB strain and then intercrossed.
[a]All DNA was injected at the final concentration of 3 ng/μl. All DNA was coinjected with φC31o mRNA at the final concentration of 48 ng/μl, except for the experiment in row 5.
[b]Both FRT and non-FRT versions of pattB-pCA-GFP (pBT316 or pBT344) were used.
[c]F0s were analyzed only as E10 or E11 embryos.
[d]F0s were analyzed either as E10 or E11 embryos or as live pups.
[e]The 6 founders with cassette exchange listed here contain pCA-GFP without the bacterial backbone; 5 more founders with cassette exchange contained only the bacterial backbone. Therefore the total number of founders with cassette exchange is 11 (29%).
[f]One F0 with site-specific insertion, also contains a random insertion.
[g]One random insertion was found in a founder that also contains a site-specific insertion.
[h]The number of random insertions may be somewhat underreported when F0 embryos were included in the analysis, as random insertions

TABLE 7

Comparisons of integration efficiencies: single vs. triple attP alleles, and mixed vs. FVB background.

| Row | Pooled rows from Table 1[a] | Strain | Background | F0 (n)[a] | SS F0 (n)[a] | Significant?[b] | SS % (from F0) |
|---|---|---|---|---|---|---|---|
| 1 | 1, 7, 8 | H11P(NVφ) | mix | 102 | 8 | ns | 7.8 |
| 2 | 2, 6, 9 | H11P3(NVφ) | mix | 164 | 18 | | 11.0 |
| 3 | 3, 10 | H11P3 | FBV N4 | 23 | 9 | p = 0.0015 | 39.1 |

Abbreviations:
SS, site-specific integration;
mix, mixed background of 129, C57BL/6 and DBA2;
FVB N4, mice of the mixed background were outcrossed for 4 generations to the FVB strain and then intercrossed.
[a]Pooled results from Table 2 for the same strain and background (regardless of the presence of the NVφ cassette) used for injections of 3-6 kb DNA. The pooling did not include Table 2 entry 4 (as the mechanism of integration may be different); entry 11 (as the DNA used is dramatically larger); entry 5 (as no RNA was coinjected); and entry 12 (as it used the Rosa26 locus).
[b]Statistical significance was evaluated using Fisher's exact test.
ns, not-significant;
α = 0.05.

Example 9

Transgene Integration into the R26 Locus

To test whether φC31-mediated integration is applicable to other genomic loci, pattB-pCA-GFP was injected into embryos homozygous for R26P3NVφ(attPx3+NVφ integrated at the Rosa26 locus) and obtained integrants (Table 1). The VASA cassette was removed from R26P3NVφ using Flpo, and homozygous R26P3 mice were created to provide a second locus for integrase-mediated transgenesis.

The integration frequency for attP-modified loci, expressed as the percentage of F0 animals was compared with site-specific integrations obtained from the total number of F0s (Table 1; see Table 3 for more details). Although on pooled data, H11P3 (three copies of shortened attP) appeared somewhat more efficient that H11P (one copy of the full length attP), the efficiencies of site-specific insertions into these two loci were statistically indistinguishable (Table 1 and Table 4, Fisher's exact test). In contrast, backcrossing the H11P3 mice to the FVB strain for 4 generations (FVB N4) significantly increased the integration efficiency to ~40% (Table 1 and Table 4; Fisher's exact test). This efficiency is comparable to or better than the efficiency of traditional transgenesis with random integration. Moreover, it is at least an order of magnitude higher than the site-specific transgenesis efficiency with pronuclear injection of zinc-finger nucleases (Meyer M et al. (2010) *Proc Natl Acad Sci USA* 107:15022).

Circular DNAs with sizes (Meyer M et al. (2010) *Proc Natl Acad Sci USA* 107:15022). Circular DNAs with sizes from 3-6 kb appeared to have similar efficiencies of integration (Table 1). Although circular DNA was used for injections, insertions at locations other than the intended attP sites (Table 1) occurred at a highly variable frequency (0-20%). In 20 out of 23 founders that transmitted their site-specific transgene to the progeny, the site-specific integrants contained a single copy transgene and did not contain a second random insertion as judged by PCR and quantitative PCR. In rare cases, when site-specific and random integration occurred in the same transgenic founder, the two integrations could be readily segregated in the F1 progeny.

TABLE 8

Step-wise efficiency of site-specific integration.

| DNA[a,b] | DNA type | DNA size (kb) | Strain | Background | Embryos injected (n) | Embryos implanted (n) | Implanted/Injected (%) | F0 (n) |
|---|---|---|---|---|---|---|---|---|
| pattB-pCA-GFP, no RNA | plasmid | ~6 | H11P3NVφ | mix | 160 | 78 | 49 | 32[d] |
| pattB-pCA-GFP | plasmid | ~6 | H11PNVφ | mix | 140 | 89 | 64 | 30[d] |
| pattB-pCA-GFP | plasmid | ~6 | H11P3NVφ | mix | 292 | 223 | 76 | 64[e] |
| pattB-pCA-GFP | plasmid | ~6 | R26P3NVφ | mix | 83 | 63 | 76 | 22[d] |
| pattB-pCA-GFP-FRT5 | plasmid | ~6 | H11P | mix | 264 | 232 | 88 | 51 |
| pattB-pCA-GFP-(FRT5)[a] | plasmid | ~6 | H11P3 | mix | 142 | 129 | 91 | 61 |
| pattB-pCA-GFP-FRT5 | plasmid | ~6 | H11P3 | FVB N4 | 50 | 43 | 86 | 8 |
| attB-pCA-GFP (MC) | minicircle | ~3 | H11P | mix | 141 | 115 | 82 | 21 |
| attB-pCA-GFP (MC) | minicircle | ~3 | H11P3 | mix | 168 | 136 | 81 | 39 |
| attB-pCA-GFP (MC) | minicircle | ~3 | H11P3 | FVB N4 | 122 | 115 | 94 | 15 |

| DNA[a,b] | F0/implanted (%) | SS (n) | SS % (from injected) | SS % (from implanted) | SS % (from F0) | R[h] (n) | R % (from implanted)[h] | R % (from F0)[h] | Experiments (n) |
|---|---|---|---|---|---|---|---|---|---|
| pattB-pCA-GFP, no RNA | 41 | 0 | 0.0 | 0.0 | 0.0 | 5 | 0.4 | 15.6 | 1 |
| pattB-pCA-GFP | 34 | 2 | 1.4 | 2.2 | 6.7 | 0 | 0.0 | 0.0 | 2 |
| pattB-pCA-GFP | 29 | 10 | 3.4 | 4.5 | 15.6 | 4 | 1.8 | 6.3 | 3 |
| pattB-pCA-GFP | 35 | 2 | 2.4 | 3.2 | 9.1 | 2 | 3.2 | 9.1 | 1 |
| pattB-pCA-GFP-FRT5 | 22 | 5[f] | 1.9 | 2.2 | 9.8 | 3[g] | 0.9 | 5.9 | 5 |
| pattB-pCA-GFP-(FRT5)[a] | 47 | 4[f] | 2.8 | 3.1 | 6.6 | 9[g] | 9.9 | 14.8 | 4 |
| pattB-pCA-GFP-FRT5 | 19 | 3[f] | 6.0 | 7.0 | 37.5 | 1[g] | 0.0 | 10.3 | 1 |
| attB-pCA-GFP (MC) | 18 | 1 | 0.7 | 0.9 | 4.8 | 1 | 0.9 | 4.8 | 4 |
| attB-pCA-GFP (MC) | 29 | 4 | 2.4 | 2.9 | 10.3 | 1 | 0.7 | 2.6 | 4 |
| attB-pCA-GFP (MC) | 13 | 6 | 4.9 | 5.2 | 40.0 | 3 | 2.6 | 20.0 | 3 |

Abbreviations:

SS, site-specific integration;

R, random integration, mix, mixed background of 129, C57BL/6 and DBA2;

FVB N4, the mice of mixed background were backcrossed for 4 generations to the FVB strain and then intercrossed.

[a]All DNA was injected at the final concentration of 3 ng/μl. All DNA was coinjected with φC31o mRNA at the final concentration of 48 ng/μl, except where indicated.

[b]pattB-pCA-GFP-FRT5 (pBT344) is a derivative of pattB-pCA-GFP (pBT316), with a single FRT5 site inserted 3' to the SV40 polyadenylation sequence, which is located 3' to GFP. attB-pCA-GFP minicircle was derived from plasmid pBT346.

Both FRT and non-FRT versions of pattB-pCA-GFP (pBT316 or pBT344) were used.

[d]F0s were analyzed only as E10 or E11 embryos.

[e]F0s were analyzed either as E10 or E11 embryos or as live pups.

[f]One F0 with site-specific insertion, also contains a random insertion.

[g]One random insertion was found in a founder that also contains a site-specific insertion.

[h]The number of random insertions may be somewhat underreported when F0 embryos were included in the analysis, as random insertions are not detectable by GFP-specific PCR if they occur in embryos that also contain site-specific insertions.

TABLE 9

Comparisons of integration efficiencies for single and triple attP alleles, and mixed and FVB background

| Strain | Background | F0 (n)[a] | SS F0 (n)[a] | Significant?[b] | SS % (from F0) |
|---|---|---|---|---|---|
| H11P(NVφ) | mix | 102 | 8 | ns | 7.8 |
| H11P3(NVφ) | mix | 164 | 18 |  | 11.0 |
| H11P3 | FVB N4 | 23 | 9 | ** (p = 0.0015) | 39.1 |

Abbreviations:
SS, site-specific integration;
mix, mixed background of 129, C57BL/6 and DBA2;
FVB N4, mice of the mixed background were backcrossed for 4 generations to the FVB strain and then intercrossed.
[a]Pooled numbers from table 1 for appropriate genotypes, regardless of the kind of injected DNA and the presence of the VASA(NVφ) cassette.
[b]Statistical significance was evaluated using Fisher's exact test.
ns, not-siginificant;
** p < 0.01.

CONCLUSION

The method of the present disclosure is considerably simpler than transgenesis using homologous recombination in ES cells and offers many technical advantages compared to the most-widely used method of random integration of transgenes via pronuclear injection. Transgenes produced from this site-specific integration method are intact, have a defined copy number and chromosomal environment, and do not disrupt endogenous genes. These properties increase the reliability of many transgenesis-based experiments and enable new ones. For example, the relationships between amino acid sequences or domain structures of a protein and its in vivo biological functions can be more reliably compared if a series of transgenes expressing different variants of a protein are expressed at the same level. The regulatory elements that control gene expression can also be systematically dissected when reporter transgenes from the same integration site are compared; subtle differences in levels or patterns of transgene expression that would be overwhelmed by positional effects and differences in copy numbers in randomly integrated transgenes can now be deciphered using site-specific integration of transgenes.

Mice have been generated that allow for integration at two defined loci, a widely used Rosa26 locus (Soriano P (1999) Nat Genet. 21:70) and a new Hipp11 locus, which support high-level ubiquitous expression of integrated transgenes. Future generation and characterization of additional transgenes and integration sites should enable tissue-specificity and inducibility of transgene expression.

This study also revealed that a neighboring tissue-specific promoter-driven transgene and plasmid's bacterial backbone affected the expression reliability of GFP transgenes driven by a ubiquitous promoter. The effect of BB has been reported in episomal transgenes, and other native bacterial sequences like the lacZ gene have been suspected to cause variegation in transgenic animals. The experiments based on site-specific integration presented above enabled one to unambiguously establish this phenomenon for single-copy chromosomally-integrated transgenes and to systematically and quantitatively characterize these effects. These studies revealed intricacies of single-copy transgene expression in vivo, emphasized the requirements for gene expression reliability in mammals including gene therapy in humans, and provided an efficient system for studying gene expression and function in vivo It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. While the subject antibody, method, and composition have been particularly shown and described with references to preferred embodiments thereof, it will be understood by those skilled in the art that various changes in form and details may be made therein without departing from the scope of the invention encompassed by the appended claims.

What is claimed is:

1. A method of inserting a polynucleotide sequence into a genome of a murine cell, comprising:
   introducing a circular nucleic acid into said murine cell, wherein said circular nucleic acid comprises said polynucleotide sequence and a first unidirectional recombination site, and
   wherein said genome of said murine cell comprises a second unidirectional recombination site at the intergenic Hipp11 (H11) locus on mouse chromosome 11;
   introducing an mRNA a nucleic acid encoding a site-specific, unidirectional recombinase into said cell; and
   maintaining said cell under conditions that facilitate recombination between said first and second unidirectional recombination sites mediated by said unidirectional recombinase, wherein said method results in a site-specific integration of said polynucleotide sequence into the genome of said murine cell.

2. The method of claim 1, wherein:
   the circular nucleic acid comprises the polynucleotide sequence flanked by a first and a second copy of the first unidirectional recombination site; and
   wherein the genome of the murine cell comprises a first and a second copy of the second unidirectional recombination site; and
   wherein the method further comprises maintaining the cell under conditions that facilitate recombination between the first copies of the first and second unidirectional recombination sites and the second copies of the first and second unidirectional recombination sites, mediated by the unidirectional recombinase, wherein the method results in a site-specific integration of the polynucleotide sequence into the genome of the murine cell.

3. The method of claim 1, wherein said murine cell is a zygote.

4. The method of claim 3, wherein said zygote grows into a mammal containing said site-specific integration in both somatic cells and germline cells.

5. The method of claim 1, wherein said unidirectional recombinase is φC31, TP901-1, or R4.

6. The method of claim 5, wherein said first and second unidirectional recombination sites are selected from wild-type attB, wild-type attP, pseudo-sites thereof, or tandem repeats thereof.

7. The method of claim 6, wherein said pseudo-attB or pseudo-attP is derived from a sequence native to a murine genome.

8. The method of claim 1, wherein said nucleic acid encoding said site-specific, unidirectional recombinase is introduced into the cell before or concurrent to said introducing a circular nucleic acid.

9. The method of claim 1, wherein the murine cell lacks a promoter sequence at or near the second unidirectional recombination site.

10. The method of claim 1, wherein the circular nucleic acid lacks a bacterial plasmid sequence.

11. The method of claim 1, wherein the polynucleotide sequence encodes a polypeptide product.

12. The method of claim 1, wherein the nucleic acid encoding the site-specific, unidirectional recombinase is an mRNA.

13. The method of claim 12, wherein first unidirectional recombination site comprises wild-type attB or tandem repeats thereof and the second unidirectional recombination site comprises wild-type attP or tandem repeats thereof and wherein the unidirectional recombinase is ϕC31.

14. The method of claim 13, wherein said murine cell is a zygote and the introducing said circular nucleic acid and said nucleic acid encoding the site-specific, unidirectional recombinase comprises injecting said circular nucleic acid and said nucleic acid encoding the site-specific, unidirectional recombinase into pronucleus of the zygote.

15. The method of claim 1, wherein the nucleic acid encoding the site-specific, unidirectional recombinase is a circular DNA.

16. The method of claim 1, wherein said murine cell is a zygote and the introducing said circular nucleic acid and said nucleic acid encoding the site-specific, unidirectional recombinase comprises injecting said circular nucleic acid and said nucleic acid encoding the site-specific, unidirectional recombinase into pronucleus of the zygote.

* * * * *

SEQUENCE LISTING

```
<160> NUMBER OF SEQ ID NOS: 37

<210> SEQ ID NO 1
<211> LENGTH: 36
<212> TYPE: DNA
<213> ORGANISM: Artificial Sequence
<220> FEATURE:
<223> OTHER INFORMATION: Unique sequence "U" from promoter of yeast his3
      gene

<400> SEQUENCE: 1
ggtgataggt ggcaagtggt attccgtaag gatatc                               36
```

```
<210> SEQ ID NO 2
<211> LENGTH: 48
<212> TYPE: DNA
<213> ORGANISM: Artificial Sequence
<220> FEATURE:
<223> OTHER INFORMATION: FRT5 site

<400> SEQUENCE: 2
gaagttccta ttccgaagtt cctattcttc aaaaggtata ggaacttc                  48

<210> SEQ ID NO 3
<211> LENGTH: 60
<212> TYPE: DNA
<213> ORGANISM: Artificial Sequence
<220> FEATURE:
<223> OTHER INFORMATION: attP site sequence

<400> SEQUENCE: 3
cgggagtagt gccccaactg gggtaacctt tgagttctct cagttggggg cgtagggtcg     60

<210> SEQ ID NO 4
<211> LENGTH: 36
<212> TYPE: DNA
<213> ORGANISM: Artificial Sequence
<220> FEATURE:
<223> OTHER INFORMATION: PR402

<400> SEQUENCE: 4
ctagcctgca ggaattaagt taacaattaa gacgtc                               36

<210> SEQ ID NO 5
<211> LENGTH: 36
<212> TYPE: DNA
<213> ORGANISM: Artificial Sequence
<220> FEATURE:
<223> OTHER INFORMATION: PR403

<400> SEQUENCE: 5
ctaggacgtc ttaattgtta acttaattcc tgcagg                               36

<210> SEQ ID NO 6
<211> LENGTH: 32
<212> TYPE: DNA
<213> ORGANISM: Artificial Sequence
<220> FEATURE:
<223> OTHER INFORMATION: PR437

<400> SEQUENCE: 6
aaccaacctt aaccgccacc atggatacct ac                                   32

<210> SEQ ID NO 7
<211> LENGTH: 70
<212> TYPE: DNA
<213> ORGANISM: Artificial Sequence
<220> FEATURE:
<223> OTHER INFORMATION: PR438

<400> SEQUENCE: 7
aataggatcc tttttttttt tttttttttt tttttttttt ctcgagtcac actttccgct     60
ttttcttagg                                                            70

<210> SEQ ID NO 8
<211> LENGTH: 69
<212> TYPE: DNA
<213> ORGANISM: Artificial Sequence
```

```
<220> FEATURE:
<223> OTHER INFORMATION: PR493

<400> SEQUENCE: 8
aaagaggtac cagttacgct agggataaca gggtaatata gcaaataatg atttttatttt      60 gactgatag                                                               69

<210> SEQ ID NO 9
<211> LENGTH: 35
<212> TYPE: DNA
<213> ORGANISM: Artificial Sequence
<220> FEATURE:
<223> OTHER INFORMATION: PR494

<400> SEQUENCE: 9
aaatactcga gagcctgctt ttttgtacaa agttg                                  35

<210> SEQ ID NO 10
<211> LENGTH: 39
<212> TYPE: DNA
<213> ORGANISM: Artificial Sequence
<220> FEATURE:
<223> OTHER INFORMATION: PR495

<400> SEQUENCE: 10
aagaagcggc cgcacaagtt tgtacaaaaa agctgaacg                              39

<210> SEQ ID NO 11
<211> LENGTH: 38
<212> TYPE: DNA
<213> ORGANISM: Artificial Sequence
<220> FEATURE:
<223> OTHER INFORMATION: PR496

<400> SEQUENCE: 11
aagaagagct ccatagtgac tggatatgtt gtgtttta                               38

<210> SEQ ID NO 12
<211> LENGTH: 37
<212> TYPE: DNA
<213> ORGANISM: Artificial Sequence
<220> FEATURE:
<223> OTHER INFORMATION: PR374

<400> SEQUENCE: 12
atgtgaggca ggagatgaga gaggaatgac tggtcac                                37

<210> SEQ ID NO 13
<211> LENGTH: 36
<212> TYPE: DNA
<213> ORGANISM: Artificial Sequence
<220> FEATURE:
<223> OTHER INFORMATION: PR432

<400> SEQUENCE: 13
gatatcctta cggaatacca cttgccacct atcacc                                 36

<210> SEQ ID NO 14
<211> LENGTH: 43
<212> TYPE: DNA
<213> ORGANISM: Artificial Sequence
<220> FEATURE:
<223> OTHER INFORMATION: PR351
```

<400> SEQUENCE: 14
aataagctag cctcgaggat atcctgtgcc ttctagttgc cag    43

<210> SEQ ID NO 15
<211> LENGTH: 30
<212> TYPE: DNA
<213> ORGANISM: Artificial Sequence
<220> FEATURE:
<223> OTHER INFORMATION: PR422

<400> SEQUENCE: 15 ccattttta gtaccctct acactcctcc    30

<210> SEQ ID NO 16
<211> LENGTH: 21
<212> TYPE: DNA
<213> ORGANISM: Artificial Sequence
<220> FEATURE:
<223> OTHER INFORMATION: Rosa3

<400> SEQUENCE: 16
ccactgaccg cacggggatt c    21

<210> SEQ ID NO 17
<211> LENGTH: 22
<212> TYPE: DNA
<213> ORGANISM: Artificial Sequence
<220> FEATURE:
<223> OTHER INFORMATION: PR395

<400> SEQUENCE: 17
gttgagggca atctgggaag gt    22

<210> SEQ ID NO 18
<211> LENGTH: 22
<212> TYPE: DNA
<213> ORGANISM: Artificial Sequence
<220> FEATURE:
<223> OTHER INFORMATION: SH176

<400> SEQUENCE: 18
tggaggagga caaactggtc ac    22

<210> SEQ ID NO 19
<211> LENGTH: 22
<212> TYPE: DNA
<213> ORGANISM: Artificial Sequence
<220> FEATURE:
<223> OTHER INFORMATION: SH178

<400> SEQUENCE: 19 ttcccttct gcttcatctt gc    22

<210> SEQ ID NO 20
<211> LENGTH: 21
<212> TYPE: DNA
<213> ORGANISM: Artificial Sequence
<220> FEATURE:
<223> OTHER INFORMATION: Rosa10

<400> SEQUENCE: 20
ctctgctgcc tcctggcttc t    21

```
<210> SEQ ID NO 21
<211> LENGTH: 21
<212> TYPE: DNA
<213> ORGANISM: Artificial Sequence
<220> FEATURE:
<223> OTHER INFORMATION: Rosa11

<400> SEQUENCE: 21
cgaggcggat cacaagcaat a                                              21

<210> SEQ ID NO 22
<211> LENGTH: 24
<212> TYPE: DNA
<213> ORGANISM: Artificial Sequence
<220> FEATURE:
<223> OTHER INFORMATION: PR425

<400> SEQUENCE: 22
ggtgataggt ggcaagtggt attc                                           24

<210> SEQ ID NO 23
<211> LENGTH: 21
<212> TYPE: DNA
<213> ORGANISM: Artificial Sequence
<220> FEATURE:
<223> OTHER INFORMATION: PR436

<400> SEQUENCE: 23
atcaactacc gccacctcga c                                              21

<210> SEQ ID NO 24
<211> LENGTH: 20
<212> TYPE: DNA
<213> ORGANISM: Artificial Sequence
<220> FEATURE:
<223> OTHER INFORMATION: PR522

<400> SEQUENCE: 24
cgatgtaggt cacggtctcg                                                20

<210> SEQ ID NO 25
<211> LENGTH: 20
<212> TYPE: DNA
<213> ORGANISM: Artificial Sequence
<220> FEATURE:
<223> OTHER INFORMATION: PR387

<400> SEQUENCE: 25
gtgggactgc tttttccaga                                                20

<210> SEQ ID NO 26
<211> LENGTH: 23
<212> TYPE: DNA
<213> ORGANISM: Artificial Sequence
<220> FEATURE:
<223> OTHER INFORMATION: PR428

<400> SEQUENCE: 26
ccgaaaagtg ccacctgaat aat                                            23

<210> SEQ ID NO 27
<211> LENGTH: 21
<212> TYPE: DNA
<213> ORGANISM: Artificial Sequence
<220> FEATURE:
<223> OTHER INFORMATION: FACS G5'
```

<400> SEQUENCE: 27
cttcaagtcc gccatgcccg a                                           21

<210> SEQ ID NO 28
<211> LENGTH: 22
<212> TYPE: DNA
<213> ORGANISM: Artificial Sequence
<220> FEATURE:
<223> OTHER INFORMATION: GFP2-Hermie

<400> SEQUENCE: 28
tccagcagga ccatgtgatc gc                                          22

<210> SEQ ID NO 29
<211> LENGTH: 20
<212> TYPE: DNA
<213> ORGANISM: Artificial Sequence
<220> FEATURE:
<223> OTHER INFORMATION: PR21

<400> SEQUENCE: 29
ctgcaaggcg attaagttgg                                             20

<210> SEQ ID NO 30
<211> LENGTH: 20
<212> TYPE: DNA
<213> ORGANISM: Artificial Sequence
<220> FEATURE:
<223> OTHER INFORMATION: PR387

<400> SEQUENCE: 30
gtgggactgc tttttccaga                                             20

<210> SEQ ID NO 31
<211> LENGTH: 20
<212> TYPE: DNA
<213> ORGANISM: Artificial Sequence
<220> FEATURE:
<223> OTHER INFORMATION: PR487

<400> SEQUENCE: 31 tcccctgaa cctgaaacat                                              20

<210> SEQ ID NO 32
<211> LENGTH: 20
<212> TYPE: DNA
<213> ORGANISM: Artificial Sequence
<220> FEATURE:
<223> OTHER INFORMATION: LL84

<400> SEQUENCE: 32
aagtcgtgct gcttcatgtg                                             20

<210> SEQ ID NO 33
<211> LENGTH: 19
<212> TYPE: DNA
<213> ORGANISM: Artificial Sequence
<220> FEATURE:
<223> OTHER INFORMATION: LL85

<400> SEQUENCE: 33
acgtaaacgg ccacaagtt                                              19

```
<210> SEQ ID NO 34
<211> LENGTH: 20
<212> TYPE: DNA
<213> ORGANISM: Artificial Sequence
<220> FEATURE:
<223> OTHER INFORMATION: IMR0015

<400> SEQUENCE: 34
caaatgttgc ttgtctggtg                                              20

<210> SEQ ID NO 35
<211> LENGTH: 20
<212> TYPE: DNA
<213> ORGANISM: Artificial Sequence
<220> FEATURE:
<223> OTHER INFORMATION: IMR0016

<400> SEQUENCE: 35
gtcagtcgag tgcacagttt                                              20

<210> SEQ ID NO 36
<211> LENGTH: 24
<212> TYPE: DNA
<213> ORGANISM: Artificial Sequence
<220> FEATURE:
<223> OTHER INFORMATION: PR488

<400> SEQUENCE: 36
gcaatagcat cacaaatttc acaa                                         24

<210> SEQ ID NO 37
<211> LENGTH: 23
<212> TYPE: DNA
<213> ORGANISM: Artificial Sequence
<220> FEATURE:
<223> OTHER INFORMATION: PR522

<400> SEQUENCE: 37
ggctatgaac taatgacccc gta                                          23
```